(12) United States Patent
Kopelman

(10) Patent No.: US 9,408,679 B2
(45) Date of Patent: Aug. 9, 2016

(54) METHOD, APPARATUS AND SYSTEM FOR USE IN DENTAL PROCEDURES

(75) Inventor: Avi Kopelman, Tenafly, NJ (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 1312 days.

(21) Appl. No.: 12/451,896

(22) PCT Filed: Jul. 2, 2009

(86) PCT No.: PCT/IL2009/000662
§ 371 (c)(1),
(2), (4) Date: Dec. 4, 2009

(87) PCT Pub. No.: WO2010/001401
PCT Pub. Date: Jan. 7, 2010

(65) Prior Publication Data
US 2010/0191510 A1    Jul. 29, 2010

Related U.S. Application Data

(60) Provisional application No. 61/129,553, filed on Jul. 3, 2008, provisional application No. 61/193,071, filed on Oct. 27, 2008.

(51) Int. Cl.
| | | |
|---|---|---|
| G06F 17/50 | (2006.01) | |
| A61C 13/00 | (2006.01) | |
| A61C 19/045 | (2006.01) | |

(52) U.S. Cl.
CPC .......... *A61C 13/0004* (2013.01); *A61C 19/045* (2013.01)

(58) Field of Classification Search
USPC ............................................................ 703/1
See application file for complete search history.

(56) References Cited

U.S. PATENT DOCUMENTS

| | | |
|---|---|---|
| 4,411,622 A | 10/1983 | Hansen |
| 5,569,033 A | 10/1996 | Michael |
| 6,099,314 A | 8/2000 | Kopelman et al. |
| 6,152,731 A | 11/2000 | Jordan et al. |
| 6,431,871 B1 | 8/2002 | Luthardt |
| 7,220,124 B2 | 5/2007 | Taub et al. |
| 7,347,690 B2 | 3/2008 | Jordan et al. |
| 2002/0031743 A1 | 3/2002 | Kim |

(Continued)

FOREIGN PATENT DOCUMENTS

| | | |
|---|---|---|
| WO | 00/08415 A1 | 2/2000 |
| WO | WO 02/102270 A1 | 12/2002 |
| WO | WO 2004/028396 A1 | 4/2004 |
| WO | 2007/010524 A2 | 1/2007 |

OTHER PUBLICATIONS

Chapuis et al. "A New System for Computer-Aided Preoperative Planning and Intraoperative Navigation During Corrective Jaw Surgery" IEEE May 2007.*

(Continued)

*Primary Examiner* — Saif Alhija
(74) *Attorney, Agent, or Firm* — Wislon Sonsini Goodrich & Rosati

(57) ABSTRACT

A method and system are provided for providing patient data useful for dental procedures, including scanning a dental structure of a patient when coupled to a geometric structure to provide a virtual model representative of the coupling and the dental structure, and relating the virtual model to a body reference of the patient.

16 Claims, 19 Drawing Sheets

(56) References Cited

U.S. PATENT DOCUMENTS

| | | |
|---|---|---|
| 2004/0015176 A1 | 1/2004 | Cosman |
| 2004/0254476 A1* | 12/2004 | Quadling et al. ............. 600/476 |
| 2005/0089822 A1 | 4/2005 | Geng |
| 2006/0001739 A1 | 1/2006 | Babayoff |
| 2007/0015111 A1 | 1/2007 | Kopelman et al. |
| 2007/0190492 A1* | 8/2007 | Schmitt ........................ 433/213 |
| 2008/0015727 A1 | 1/2008 | Dunne et al. |
| 2008/0064008 A1 | 3/2008 | Schmitt |

OTHER PUBLICATIONS

Rosenstiel, et al., "History, examination, diagnosis, and prognosis: planning and preparation", Contemporary Fixed Prosthodontics, second edition, pp. 19-36.

European search report and opinion dated Apr. 13, 2016 for EP Application No. 09773056.8.

* cited by examiner

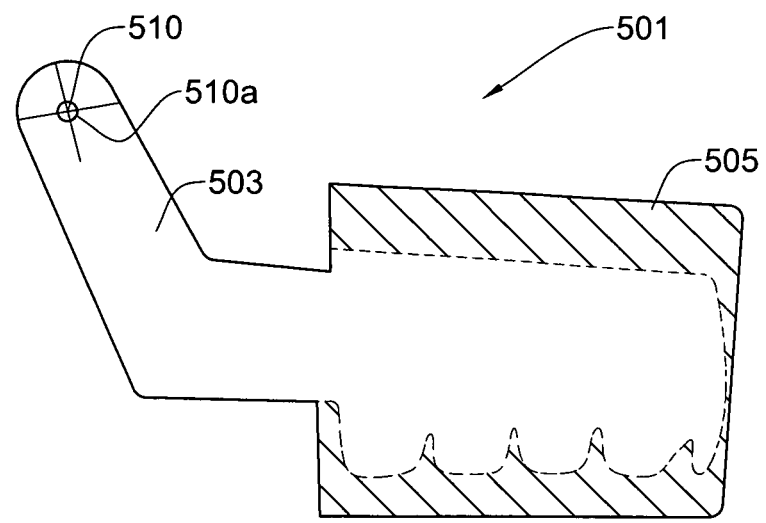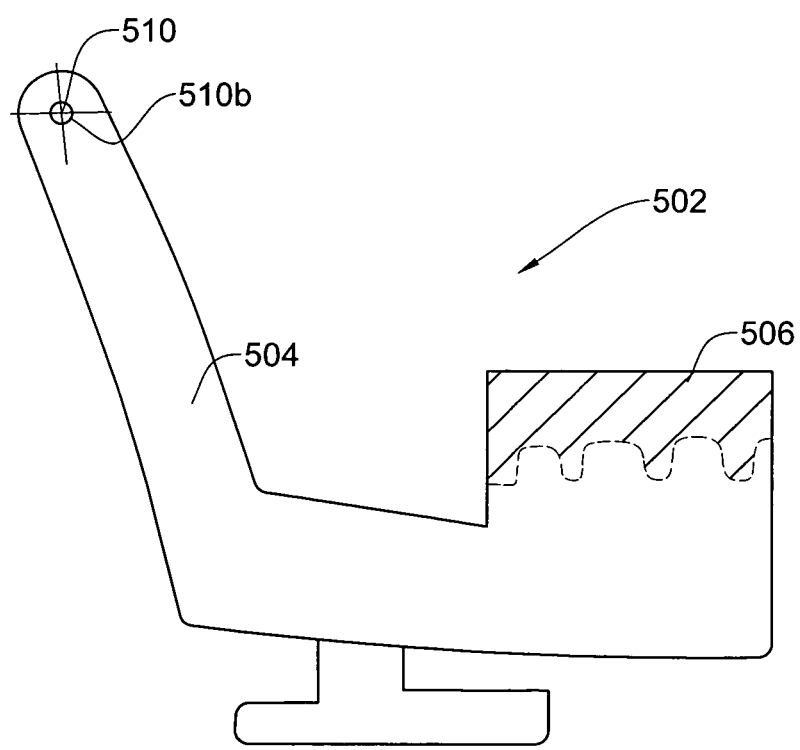
FIG. 9

METHOD, APPARATUS AND SYSTEM FOR USE IN DENTAL PROCEDURES

This is a National Phase Application filed under 35 U.S.C. 371 as a national stage of PCT/IL2009/000662, filed on Jul. 2, 2009, an application claiming the benefit under 35 USC 119 (e) of U.S. Provisional Application No. 61/129,553, filed on Jul. 3, 2008, and claiming the benefit under 35 USC 119(e) of U.S. Provisional Application No. 61/193,071, filed on Oct. 27, 2008, the content of each of which is hereby incorporated by reference in its entirety.

FIELD OF THE INVENTION

This invention relates to dental data and dental procedures, in particular with reference to apparatuses, systems and methods associated with dental data and dental procedures, in particular dental articulation and dental restorations.

BACKGROUND OF THE INVENTION

Articulators are well known dental devices which attempt to replicate the movement of the lower jaw relative to the upper jaw about the Temporomandibular Joint (TMJ) in a patient-specific manner. Typically, plaster models of the patient's upper and lower teeth arches are mounted to the articulator with respect to its hinge axis in a manner simulating that of the real teeth arches with respect to the patient's TMJ joint. Traditionally, physical impressions of the dental arches are provided, which are then used for casting the plaster models. In addition, a bite impression is obtained with a wax bite plate, which records the relative positions of the upper and lower arches.

A mechanical facebow with a bite fork is often used for obtaining patient-specific measurements which are then used to set up the plaster model in a particular articulator. In particular, the spatial orientation of the patient's maxillary arch with respect to the ear canals is duplicated by the facebow. The facebow is engaged to the ear canals via an ear canal insertion portion. Then, a bite fork with impression material is brought into engagement with the maxillary teeth, and a jig connects the bite fork via its arm to the facebow. The facebow and bite fork combination are then mechanically rigidly coupled to the articulator, such that the ear canal insertion portions are in the corresponding alignment with the pivot axis of the articulator. The plaster models are mounted to the articulator so as to engage and thus match the position of the bite fork, and plaster filling is provided between each plaster model and the respective articulator arm. However, this is a complicated and time consuming process, and which requires expert handling. Once the models are mounted, the facebow and bite fork can be removed.

The articulator mounted with the plaster models can be made use of for a large number of orthodontic, prosthodontic and other dental applications. For example, dental restoration procedures often make use of articulators to design and test prostheses before implantation in a patient.

By way of general background, U.S. Pat. No. 6,152,731 discloses a computer implemented method that includes providing a first set of digital data corresponding to an upper arch image of at least a portion of an upper dental arch of a patient, providing a second set of digital data corresponding to a lower arch image of at least a portion of a lower dental arch of the patient, providing bite alignment data representative of the spatial relationship between the upper dental arch and the lower dental arch of the patient, and aligning the upper and lower arch images relative to one another based on the bite alignment data until an aligned upper and lower arch image is attained. The aligned upper and lower arch images are moved towards each other until a first contact point is detected and at least one of the upper and lower arch images is moved relative to the other in one or more directions to a plurality of positions for determining optimal occlusion position of the lower and upper dental arches.

SUMMARY OF THE INVENTION

The term "virtual model" is used herein synonymously with "numerical entity", 3D model, computer generated model, and other such terms, and relates to a virtual representation in a computer environment of a real (physical) object, for example a dentition or part thereof or at least a part of intraoral cavity, or of a real (physical) model thereof, for example.

The term "scanning" and its analogues refer to any procedure directed at obtaining 3D topographic data of a surface, particularly of a dental surface, and thus includes: mechanical or contact methods, typically based on 3D probes for example; non-contact methods, in particular optical methods, including for example confocal methods, for example as disclosed in WO 00/08415, the contents of which are incorporated herein in their entirety by reference; or indeed any other suitable method. The term "scanner" refers to any suitable device or system that provides a scanning operation.

The term "display" and its analogues refer to any means or method for delivering a presentation, which may include any information, data, images, sounds, etc, and thus the delivery may be in visual and/or audio form, for example an electronic audio/visual image, printed matter, and so on.

While the term "dental structure" herein is taken to include, in addition to a patient's dentition or part thereof or, including part of a tooth, including a preparation, a tooth or a number of teeth, or one or both dental arches, dental restorations or prostheses, or at least a part of the intraoral cavity, it is also taken to include a real (physical) model of part of a tooth, including a preparation, a tooth or a number of teeth, or one or both dental arches, dental restorations or prostheses, or at least a part of the intraoral cavity, for example, the real model being a positive model, or a negative model (impression) or a composite positive-negative model.

According to a first aspect of the invention there is provided a method for providing a spatial relationship of at least part of a dental structure of a patient with respect to a body reference of the patient, comprising
 (a) generating a first virtual model representative of at least a part of said dental structure coupled with a geometric structure in a first spatial relationship therewith, wherein a second spatial relationship between said geometric structure and said body reference is known or determinable;
 (b) determining the spatial relationship between said part of said dental structure and said body reference from said first spatial relationship and said second spatial relationship.

The term "geometric structure" is used interchangeably herein with "geometrical structure", and includes any suitable structure having a geometric form that is substantially fixed in geometry and exposed in conjunction with the part of a dental structure, at least when implementing, said method.

The method at least according to the first aspect of the invention, may optionally further comprise one or more of the following features in any suitable combination.

In some embodiments, step (a) comprises scanning said part of said dental structure coupled with said geometric structure with a suitable scanner to obtain said first virtual model. In other embodiments, said geometric structure further comprises a physical impression of said part of said dental structure, and step (a) comprises scanning said impression coupled with said geometric structure with a suitable scanner to obtain a second virtual model, and generating said first virtual model from said second virtual model; step (a) may comprise providing a third virtual model representative of said part of said dental structure, and registering said third virtual model with said second virtual model and generating therefrom said first virtual model.

The method may further comprise providing a virtual model of a second dental structure that includes said part of said first-mentioned dental structure, registering said virtual model of said second dental structure with said first virtual model, and determining the spatial relationship between said second dental structure and said body reference from said first spatial relationship, said second spatial relationship.

The scanner may comprise, for example, an optical scanner, and optionally operation of said scanner is based on confocal imaging techniques. For example, the scanner may comprise:
  a probing member with a sensing face;
  first illumination means for providing a first array of incident light beams transmitted towards the structure along an optical path through said probing unit to generate illuminated spots on said portion along said depth direction, wherein said first array is defined within said reference array;
  a light focusing optics defining one or more focal planes forward said probing face at a position changeable by said optics, each light beam having its focus on one of said one or more focal plane;
  a translation mechanism for displacing said focal plane relative to the structure along an axis defined by the propagation of the incident light beams;
  a first detector having an array of sensing elements for measuring intensity of each of a plurality of light beams returning from said spots propagating through an optical path opposite to that of the incident light beams;
  a processor coupled to said detector for determining for each light beam a spot-specific position, being the position of the respective focal plane of said one or more focal planes yielding maximum measured intensity of the returned light beam, and based on the determined spot-specific positions, generating data representative of the topology of said portion.

In at least some embodiments, the body reference may be at least one of the ear canals, including an axis coaxial and through the two ear canals of the patient, and/or the TMJ of the patient. Step (a) may include:
  providing said geometric structure in the form of a facebow apparatus having a first facebow part coupled to a second facebow part via a coupling, such as a mechanical coupling for example, that enables the spatial relationship between the first facebow part and the second facebow part to be selectively adjusted,
  setting said first facebow part in a fixed spatial relationship with respect to said part of said dental structure to define said first spatial relationship, and
  setting said second facebow part in a fixed first facebow spatial relationship with respect to said body reference and in a fixed second facebow spatial relationship with respect to said first facebow part via said coupling to define said second spatial relationship.

In other words, step (a) may include:
  providing said geometric structure in the form of a facebow apparatus having a first facebow part coupled to a second facebow part via a coupling, such as a mechanical coupling for example, that enables the spatial relationship between the first facebow part and the second facebow part to be selectively adjusted,
  coupling the facebow apparatus to said part of said dental structure by setting said first facebow part in a fixed spatial relationship with respect to said part of said dental structure to define said first spatial relationship, and
  manipulating said second facebow part with respect to said first facebow part via said coupling thereby setting said second facebow part in a fixed first facebow spatial relationship with respect to said body reference and in a fixed second facebow spatial relationship with respect to said first facebow part via said coupling to define said second spatial relationship.

The said first facebow part may be in the form of a bite fork apparatus, for example, and comprises a bite plate mounted to said coupling, and said coupling may be configured for providing at least two degrees of freedom for said bite plate with respect to said second facebow part, which operates substantially as a rigid body with respect to said coupling, wherein step (a) comprises manipulating said first facebow part with respect to said second facebow part via said coupling until said bite plate is abutted to at least one tooth arch of the patient comprising said part of said dental structure, while concurrently setting said second facebow part at fixed said first facebow spatial relationship with respect to said body reference. In at least one example, said degrees of freedom include a translation and a rotation of said bite plate with respect to said second facebow part. In at least another example, said degrees of freedom include a first rotation, a second rotation, and a rotation of said bite plate with respect to said second facebow part, and said first rotation and said second rotation may comprise respective rotational axes that are mutually orthogonal.

Step (a) may comprise generating a virtual model of a first zone of said facebow apparatus comprising at least a portion of said coupling sufficient to indicate the relative position and orientation of said biteplate with respect to said second facebow part, and providing a spatial relationship between said body reference and said coupling, and determining said second facebow spatial relationship from said first zone virtual model and said spatial relationship between said body reference and said coupling. The said first zone virtual model may be generated by scanning said first zone with said scanner or with another suitable scanner. The second facebow spatial relationship may comprise a geometrical relationship including a position and orientation of said coupling with respect to a facebow reference axis associated with said second facebow portion, wherein in step (a) said facebow reference axis is aligned with the ear canals or the patient or the TMJ of the patient.

Said spatial relationship between said body reference and said coupling may be provided by scanning sufficient portions of the second facebow portion to enable reconstruction of a virtual model thereof, sufficient to define said spatial relationship between said body reference and said coupling.

Alternatively, step (a) may comprise generating at least a first partial virtual model of a first zone of said facebow apparatus comprising said part of said dental structure and a portion of said biteplate coupled thereto, and generating a second partial virtual model of a second zone of said facebow apparatus comprising at least a portion of said coupling sufficient to indicate the relative position and orientation of said biteplate with respect to said second facebow part, and determining said second facebow spatial relationship from said first and second partial virtual models. The said first partial virtual model and said second partial virtual model are generated by respectively scanning said first zone and said second zone with said scanner or with another suitable scanner. The second facebow spatial relationship may comprise a geometrical relationship including a position and orientation of said coupling with respect to a facebow reference axis associated with said second facebow portion, wherein in step (a) said facebow reference axis is aligned with the ear canals or the patient or the TMJ of the patient.

In at least some embodiments, the body reference is a midsagittal plane of the patient. Step (a) may include:

provising said geometric structure in the form of a biteplate apparatus having a first biteplate part coupled to a second biteplate part via a coupling that enables an orientation between the first biteplate part and the second biteplate part to be selectively adjusted, setting said first biteplate part in a fixed spatial relationship with respect to said part of said dental structure to define said first spatial relationship, and setting said second biteplate part in a fixed first biteplate spatial relationship with respect to said body reference and in a fixed second biteplate spatial relationship with respect to said first biteplate part via said coupling to define said second spatial relationship.

In other words, step (a) may include:

providing said geometric structure in the form of a biteplate apparatus having a first biteplate part coupled to a second biteplate part via a coupling that enables an orientation between the first biteplate part and the second biteplate part to be selectively adjusted, coupling the biteplate apparatus to said part of said dental structure by setting said first biteplate part in a fixed spatial relationship with respect to said part of said dental structure to define said first spatial relationship, and manipulating said second biteplate part with respect to said first biteplate part via said coupling thereby setting said second biteplate part in a fixed first biteplate spatial relationship with respect to said body reference and in a fixed second biteplate spatial relationship with respect to said first biteplate part via said coupling to define said second spatial relationship.

The second biteplate part may be aligned with said body reference. Step (a) may comprise manipulating said first biteplate part with respect to said second biteplate part via said coupling until said first biteplate part is abutted to at least one tooth arch of the patient comprising said part of said dental structure, while concurrently setting said second biteplate part at fixed said first biteplate spatial relationship with respect to said body reference.

Step (a) may comprise generating a virtual model of a first zone of said biteplate apparatus comprising at least a portion of said coupling sufficient to indicate the relative position and orientation of said first biteplate part with respect to said second biteplate part, and providing a spatial relationship between said body reference and said coupling, and determining said second biteplate spatial relationship from said first zone virtual model and said spatial relationship between said body reference and said coupling. The said first zone virtual model may be generated by scanning said first zone with said scanner or with another suitable scanner.

Step (a) may comprise generating at least a first partial virtual model of a first zone of said biteplate apparatus comprising said part of said dental structure and a portion of said first biteplate part coupled thereto, and generating a second partial virtual model of a second zone of said biteplate apparatus including at least a portion of said coupling sufficient to indicate the relative position and orientation of said first biteplate part with respect to said second biteplate part, and determining said second biteplate spatial relationship from said first and second partial virtual models. The said first partial virtual model and said second partial virtual model may be generated by respectively scanning said first zone and said second zone with said scanner or with another suitable scanner.

Optionally, at least said first virtual model further comprises colour data representative of said part of said dental structure.

The said body reference excludes a dental structure or the intra-oral cavity.

According to a variation of the first aspect of the invention there is provided a method for providing a spatial relationship of a dental structure of a patient with respect to a body reference of the patient, comprising coupling a geometrical structure to said dental structure in a known or determinable geometrical relationship with respect to said body reference, said geometrical structure having known or determinable geometrical properties;

scanning at least a part of said dental structure coupled with said geometric structure to generate a composite virtual model thereof;

determining said spatial relationship from said virtual model, said geometrical properties and said geometrical relationship.

According to another variation of the first aspect of the invention there is provided a method for providing patient data useful for dental procedures, comprising scanning a dental structure of a patient when coupled to a geometric structure to provide a virtual model representative of said coupling and said dental structure, and relating said virtual model to a body reference of the patient.

Said body reference excludes a dental structure.

According to another variation of the first aspect of the invention there is provided a method for providing a spatial relationship of a dental structure of a patient with respect to a body reference of the patient, comprising generating a first virtual model representative of at least a part of said dental structure coupled with a geometric structure in a first spatial relationship therewith, wherein a second spatial relationship between said geometric structure and said body reference is known or determinable, wherein said first virtual model is generated by scanning said part of said dental structure coupled with said geometric structure with a suitable scanner;

determining the spatial relationship between said part of said dental structure and said body reference from said first spatial relationship and said second spatial relationship.

Said body reference excludes a dental structure.

The method according to at least one of the above variations of first aspect of the invention, may optionally further comprise one or more of the features listed above for the method according to the first aspect of the invention, mutatis mutandis, in any suitable combination.

According to the first aspect of the invention, the determined spatial relationship between said part of said dental structure and said body reference may be used in a suitable dental procedure, for example a prosthodontic procedure, an orthodontic procedure, a dental articulation procedure, and so on.

According to the first aspect of the invention, the aforementioned methods may be implemented by means of a suitable computer.

According to a second aspect of the invention there is provided a method for providing a spatial relationship of at least a part of dental structure of a patient with respect to a body reference of the patient comprising generating a first virtual model representative of said at least a part of said dental structure coupled with said body reference, and determining said relationship from said first virtual model.

For example, said body reference comprises an external mouth structure of the patient, for example at least one of the lips of the patient in a predetermined state. For example, said predetermined state constitutes smiling by the patient, wherein said at least one lip defines a smile line of the patient. In at least some embodiments, said dental structure includes at least one dental preparation that is visually coupled to said body reference, and the method may further comprise generating a prosthesis virtual model representative of a prosthesis configured for mounting to a respective said preparation, wherein a cusp line of said prosthesis virtual model is aligned to match said smile line.

Alternatively, the body reference may comprise the TMJ or ear canals of the patient, and the first virtual model comprises this body reference as well as a zone of the head of the patient including the body reference and extending therefrom to the said part of dental structure of a patient in a contiguous manner.

The method according to the second aspect of the invention may further comprise providing a virtual model of a second dental structure that includes said part of said first-mentioned dental structure, and determining the spatial relationship between said second dental structure and said body reference from said first spatial relationship, said second spatial relationship, and registering said virtual model of said second dental structure with said first virtual model. Said virtual model is generated by scanning said part of said dental structure coupled with said body reference with a suitable scanner. For example, said scanner may be an optical scanner, and optionally operation of said scanner may be based on confocal imaging techniques. Such a scanner may comprise, for example:

- a probing member with a sensing face;
- first illumination means for providing a first array of incident light beams transmitted towards the structure along an optical path through said probing unit to generate illuminated spots on said portion along said depth direction, wherein said first array is defined within said reference array;
- a light focusing optics defining one or more focal planes forward said probing face at a position changeable by said optics, each light beam having its focus on one of said one or more focal plane;
- a translation mechanism for displacing said focal plane relative to the structure along an axis defined by the propagation of the incident light beams;
- a first detector having an array of sensing elements for measuring intensity of each of a plurality of light beams returning from said spots propagating through an optical path opposite to that of the incident light beams;
- a processor coupled to said detector for determining for each light beam a spot-specific position, being the position of the respective focal plane of said one or more focal planes yielding maximum measured intensity of the returned light beam, and based on the determined spot-specific positions, generating data representative of the topology of said portion.

Optionally, at least said virtual model further comprises colour data representative of said part of said dental structure coupled with said body reference.

Said body reference may be, for example, at least one of an imaginary point, line or zone on the patient's face, the method further comprising marking said respective point, line or zone with a material that has optical contrast with the neighbouring portions of the face thereto. For example, said body reference comprises a said line aligned with the midsagittal plane of the patient.

Said body reference excludes a dental structure.

According to a third aspect of the invention, there is provided an apparatus for use in providing a spatial relationship of a dental structure of a patient with respect to a body reference of the patient, comprising a geometrical structure comprising a first part alignable with said body reference, and a second part that in use is coupled with said dental structure, wherein said body reference excludes the ear canals or TMJ of the patient.

For example, said body reference is a sagittal plane of the patient.

Said second part may comprise a bite plate configured for being abutted with respect to a dental arch comprising said dental structure, and said first part comprises an arm pivotably mounted to said bite plate such that in operation of said apparatus, said bite plate may be received in the intra-oral cavity of the patient abutted to said dental arch, while said arm remains outside the intra oral cavity.

The apparatus may be configured for enabling said arm to be aligned with a midsagittal plane of the patient when said bite plate is abutted with respect to the dental arch. The first part may comprise a first strip alignable with said body reference, and wherein said second part comprises a second strip that in use of the apparatus is superposed over the open mouth of the patient such as to optically couple the second strip with said dental structure, and wherein said first strip and said second strip are joined to one another in a known or determinable manner via an interconnecting portion. For example, said interconnecting portion may comprise a piece of sheet material having an opening sized to enable the nose of the patient to protrude therefrom when the apparatus is in use.

Alternatively, said first part comprises a frame that is configured to be centered over the eyes of the patient when in use, and wherein said second part comprises a second strip that in use of the apparatus is superposed over the open mouth of the patient such as to optically couple the second strip with said dental surfaces, and wherein said frame and said second strip are joined to one another in a known or determinable manner via an interconnecting portion. For example, said frame may comprise a piece of sheet material having an opening sized to enable the nose of the patient to protrude therefrom when the apparatus is in use. Optionally, the apparatus may further comprise side elements for resting said apparatus on the ears of the patient, and a bridge portion for resting on the nose of the patient.

According to a variation of the third aspect of the invention there is provided an apparatus for use in providing a spatial relationship of a dental structure of a patient with respect to a body reference of the patient, comprising a geometrical structure comprising a first part coupled to a second part, said first part being alignable with said body reference, and said second part being configured for being coupled to said dental structure in operation of said apparatus, said second part being further configured to provide a portion that is optically exposed with respect to said dental structure when coupled thereto, said optically exposed portion being configured for enabling a position and orientation of the second part with respect to the dental structure to be determined based on a virtual model that may be generated by suitably scanning said second part when coupled to said dental structure.

Said second part may comprise a biteplate, and said exposed portion may comprise indicia that facilitate said determination of said position and orientation of the second part with respect to the dental structure. The visually exposed part may comprise at least one projection outwardly extending from a periphery of said bite plate.

For example, said apparatus may be configured to provide at least one degree of freedom between said first part and said second part.

Said first part may comprise a bracket in the form of a U having a pair of arm portions spaced by a base portion, the arm portions comprise means for engaging the ear canals of the patient at a reference axis of the first part, and said bite plate is connected to the base portion via a coupling configured for providing at least two degrees of freedom between the bite plate and the base portion.

Said coupling may be configured for enabling translation and a rotation of said bite plate with respect to said base portion. Alternatively, said coupling may be configured for enabling a first rotation and a second rotation of said bite plate with respect to said second facebow part, wherein said first rotation is independent of said second rotation; said first rotation and said second rotation may comprise respective rotational axes that are mutually orthogonal.

The first part may further comprise visual indicators that facilitate determination of a plane including said reference axis and passing through one of said first axis and second axis.

Optionally, said geometrical structure further comprises indicators which are adjustable to indicate a position of a body part or body reference axis or a body reference plane with respect to the first part or the second part when the apparatus is in use.

According to a fourth aspect of the invention, there is provided a system for providing a spatial relationship of a dental structure of a patient with respect to a body reference of the patient, comprising:
  at least one suitable scanner;
  a computer system configured for operating according to the method according to the first or second aspect of the invention or variations thereof;
  apparatus for use in providing said spatial relationship according to the apparatus according to the third aspect of the invention or variations thereof.

According to a fifth aspect of the invention, there is provided an adaptor for use with a dental articulator having a pair of articulator arms hinged at an articulator axis, the adaptor comprising a base portion a spacer element and a model mounting arrangement, wherein the base portion is configured for mounting to an a respective said arm of the articulator, wherein the model mounting arrangement is configured for enabling a respective dental model of part or of the full respective dental arch to be mounted thereonto according to mounting features provided in the respective model, and wherein said spacer portions rigidly interconnect the base part to the model mounting arrangement such as to provide a known spatial relationship between the articulator axis and the model when mounted to the model mounting arrangement.

According to the fifth aspect of the invention, there is also provided a dental articulator comprising at least one said adaptor.

According to a sixth aspect of the invention, there is provided a machining blank for producing a physical dental model corresponding to the jaw or maxilla of the patient, comprising a blank body configured for enabling a respective a dental arch model to be machined produced therefrom via a material removal operation, and, the blank comprising an integral arm portion having an identifiable hinge position, wherein said blank body is configured for enabling the produced dental arch model to be spatially located with respect to the hinge position in a manner corresponding to the spatial location of the respective dental arch with respect to the hinge axis of a patient's jaw hinge.

According to the sixth aspect of the invention, there is also provided a physical dental model corresponding to the jaw or maxilla of the patient, comprising a respective dental arch model and an integral arm portion having an identifiable hinge position, wherein said dental arch model is spatially located with respect to the hinge position in a manner corresponding to the spatial location of the respective dental arch with respect to the hinge axis of a patient's jaw hinge.

For example, the physical dental model may be integrally produced from a suitable blank via a material removal operation or may be integrally produced via a suitable rapid prototyping operation.

According to another aspect of the invention there is provided a method for providing a spatial relationship of an in vivo dental surface of a patient with respect to a reference plane or axis of the patient, comprising generating a virtual model of at least a part of said dental surface coupled with a structure in a fixed spatial relationship therewith, wherein the spatial relationship between said structure and said reference plane or said reference axis is known or determinable. In particular, said part of said dental surface is optically coupled with said structure.

According to another aspect of the invention there is provided a method for providing data for facilitating dental procedures, comprising:
  providing a first virtual model representative of at least a portion of the intra-oral cavity of a patient;
  providing a second virtual model, representative of at least one structure coupled to the portion of the intra-oral cavity, said structure defining at least one spatial parameter of interest associated with a dental procedure;
  determining a spatial disposition of the first virtual model with respect to the second virtual model; and
  generating, from this spatial disposition, data representative of a spatial relationship between said first virtual model and said at least one spatial parameter of interest.

The method may further comprise applying said generated data to a dental procedure.

According to another aspect of the invention there is provided a system for providing data for facilitating dental procedures, comprising a scanner, a computer system configured for carrying out the method according to at least the aforementioned aspects of the invention.

According to another aspect of the invention there is provided a dental articulator as disclosed herein.

According to another aspect of the invention there is provided an apparatus for use in providing a spatial relationship of an in vivo dental surface of a patient with respect to a reference plane or axis of the patient, comprising a structure comprising a first part alignable with said reference plane or axis, and a second part that in use is optically coupled with said dental surface. The reference plane or axis may comprise any one of a sagittal plane or midsagittal plane of the patient, for example.

According to one embodiment, the apparatus is a bite plate apparatus for use in providing a spatial relationship of an in vivo dental surface of a patient with respect to said reference plane or axis of the patient, comprising a bite plate portion hingedly mounted to a vertical plate portion about a hinge, wherein the vertical plate portion is pivotable about said hinge to be aligned with a sagittal plane of a patient, when the bite plate portion is in contact with at least some cusp tips of the upper arch of the patient.

According to another embodiment, the first portion comprises a first strip alignable with said reference plane or axis, and wherein said second portion comprises a second strip that in use of the apparatus is superposed over the open mouth of the patient such as to optically couple the second strip with said dental surfaces, and wherein said first strip and said second strip are joined to one another in a known or determinable manner via an interconnecting portion. The interconnecting portion may comprise a piece of sheet material having an opening sized to enable the nose of the patient to protrude therefrom when the apparatus is in use.

According to another embodiment, the first portion comprises a frame that is configured to be centered over the eyes of the patient when in use, and wherein said second portion comprises a second strip that in use of the apparatus is superposed over the open mouth of the patient such as to optically couple the second strip with said dental surfaces, and wherein said frame and said second strip are joined to one another in a known or determinable manner via an interconnecting portion. The frame may comprise a piece of sheet material having an opening sized to enable the nose of the patient to protrude therefrom when the apparatus is in use. The apparatus may further comprise side elements for resting said apparatus on the ears of the patient, and a bridge portion for resting on the nose of the patient.

According to another aspect of the invention there is provided an adaptor for use with a dental articulators, comprising a base portion a spacer element and a model mounting arrangement, wherein the base portion is configured for mounting to an arm of the articulator, wherein the model mounting arrangement is configured for enabling a respective dental model of part or of the full respective dental arch (upper or lower) to be mounted thereonto according to mounting features provided in the respective model, and wherein said spacer portions rigidly interconnect the base part to the model mounting arrangement such as to provide a known spatial relationship between the articulator axis and the model when mounted to the model mounting arrangement.

According to another aspect of the invention there is provided a machining blank, made from a suitable machinable material, for enabling a dental model to be machined therefrom, the blank comprising an integral arm portion having an identifiable hinge position corresponding to the hinge axis of a patient's jaw hinge.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 9 illustrates in side view blanks for producing tooth models with integral articulator arms.

DETAILED DESCRIPTION OF EMBODIMENTS

According to a first aspect of the present invention there is provided a system and method for use in dental procedures.

Figure 1:
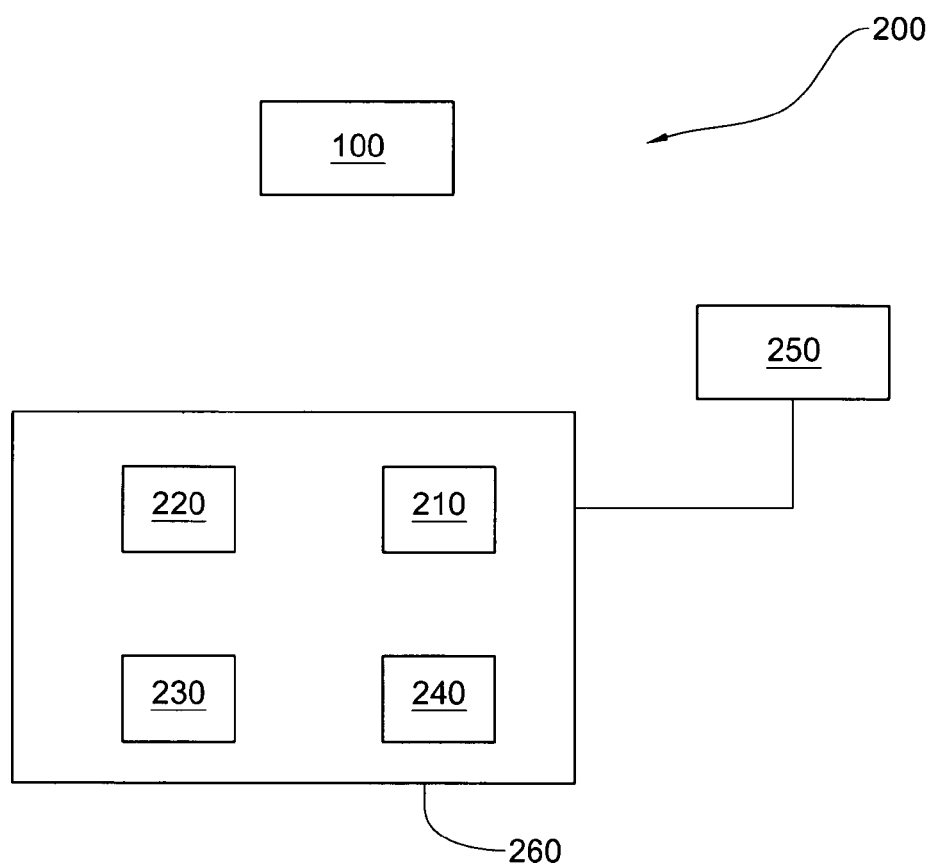
FIG. 1 is a schematic illustration of a system according to an embodiment of the invention.
Figure 5:
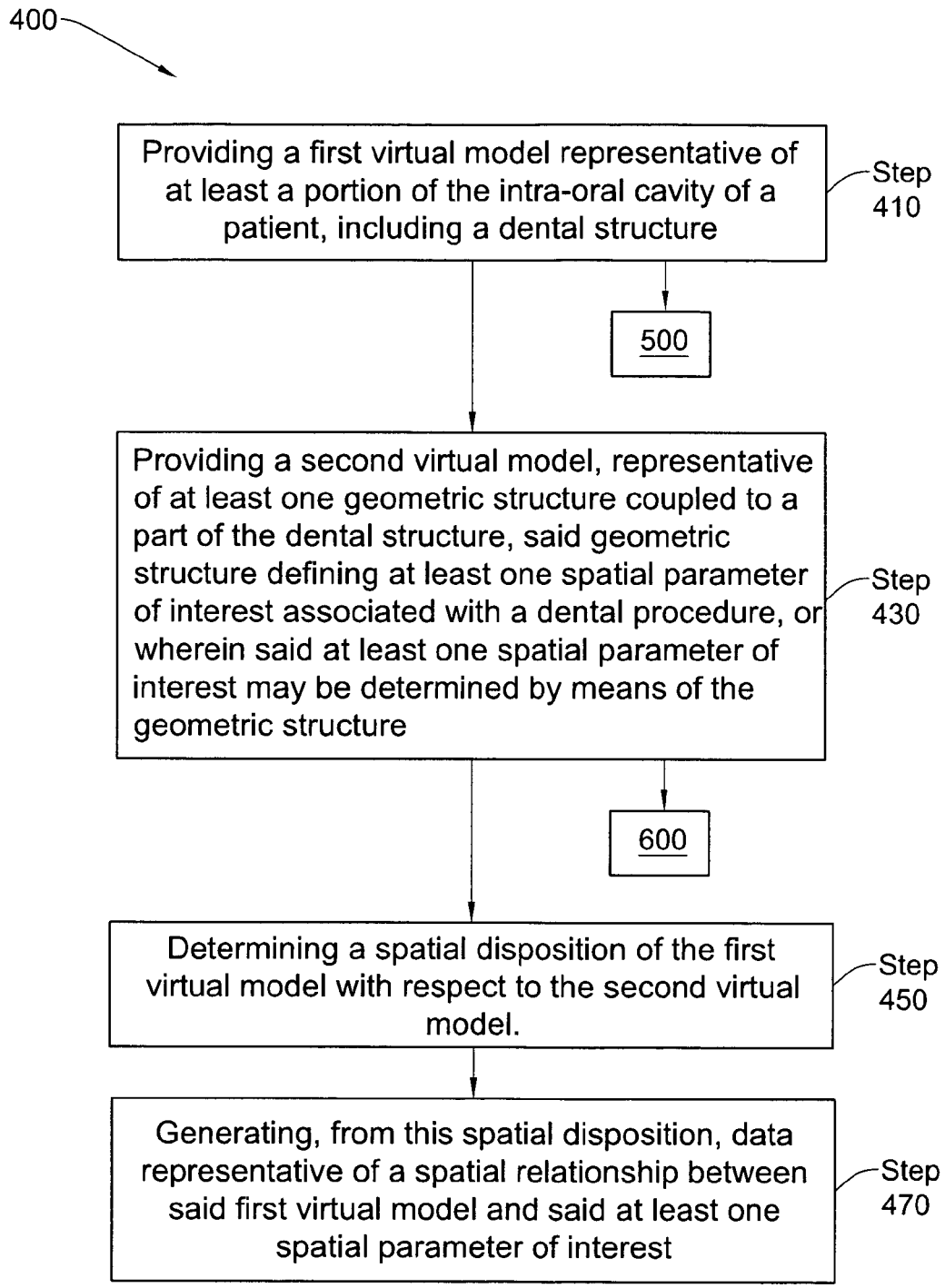
FIGS. 5, 5(*a*) 5(*b*) are schematic illustrations of a method according to embodiments of the invention.
Figure 5A:
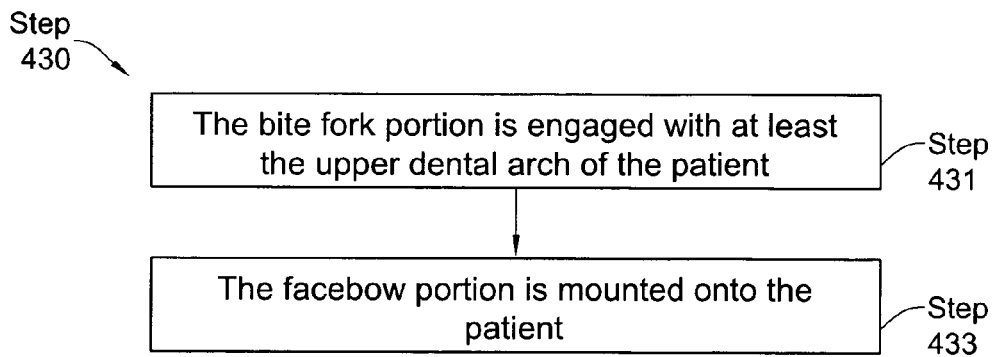
Figure 5B:
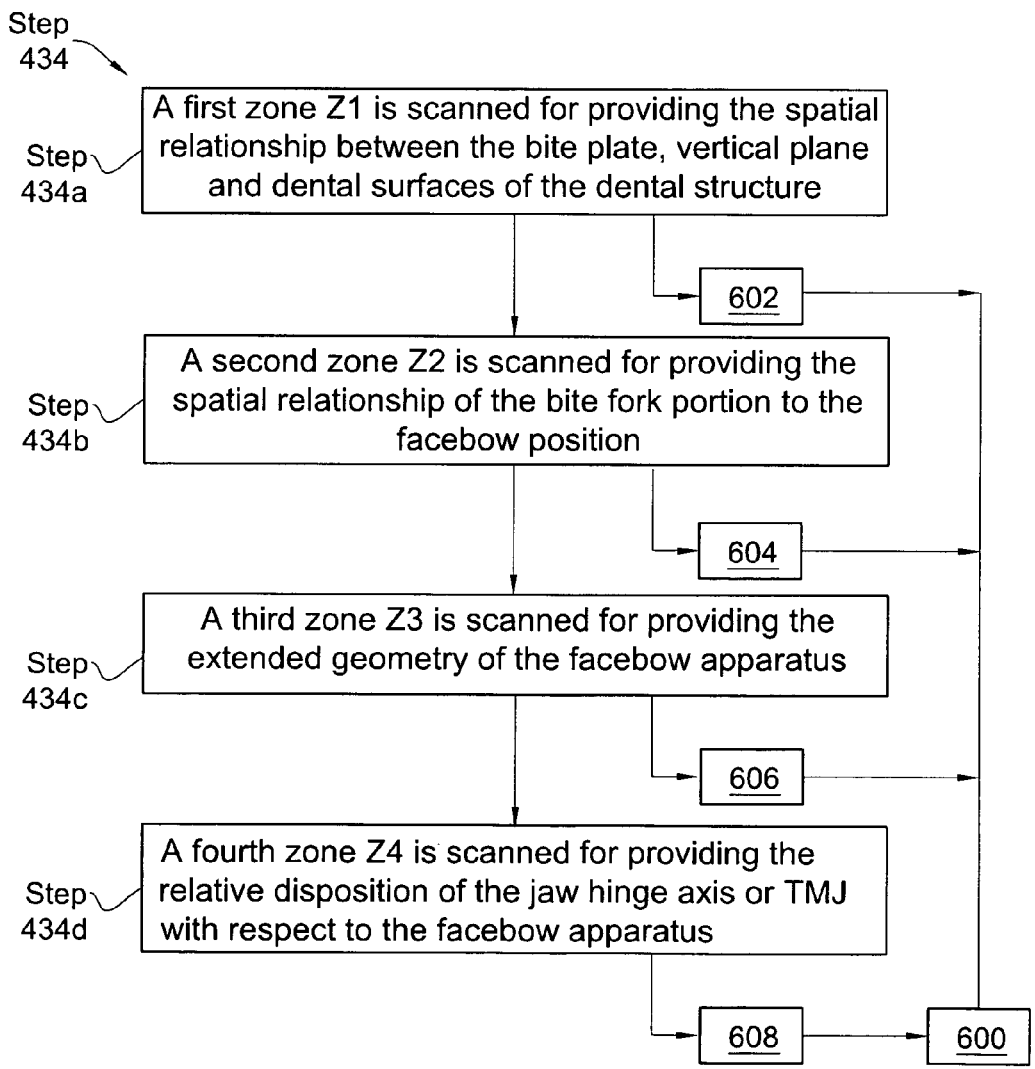

FIG. 5 illustrates a block diagram of a process 400 for providing data according to an embodiment of the invention, and FIG. 1 illustrates the main elements of a system 200 for carrying out the method according to an embodiment of the invention.

The system 200 typically comprises a scanner 250, a geometric structure in the form of a facebow apparatus 100, and a microprocessor or any other suitable computer system 260.

The computer system 260 comprises an input interface or module 210 such as a keyboard, mouse, tablet, and so on, an output device or display means or module 220, typically a screen or monitor but may additionally or alternatively include a printer, or any other display system, a computer processing unit or module 230 such as for example a CPU, and a memory 240.

The scanner 250 is configured for providing surface data of structures, in particular dental surfaces of dental structures, of other tissue surfaces of the face and head of a patient, and of the facebow apparatus or other geometric structures, and is also operatively connected to the computer system 260 and interacts therewith. The computing system 260 is suitably programmed for reconstructing such surfaces from the surface data provided, to provide a corresponding virtual model of the structure scanned by the scanner. Such a scanner may comprise, for example, any suitable non-contact scanner, for example an optical scanner. By way of non-limiting example, the scanner 250 may include a probe for determining three dimensional structure by confocal focusing of an array of light beams, for example as marketed under the name of iTero by Cadent Ltd., or as disclosed in WO 00/08415, the contents of which are incorporated herein in their entirety. Alternatively, the required scanning may be accomplished using any other suitable scanning apparatus, for example comprising a hand held probe.

Optionally, color data of the intraoral cavity may also provided together with the 3D data, to provide corresponding virtual model that comprise spatial (3D) as well as color information of the structures scanned, such as for example of dental surfaces. Examples of such scanners are disclosed in US 2006-0001739, and which is assigned to the present Assignee. The contents of the aforesaid co-pending application are incorporated herein by reference in their entirety.

Figure 2:
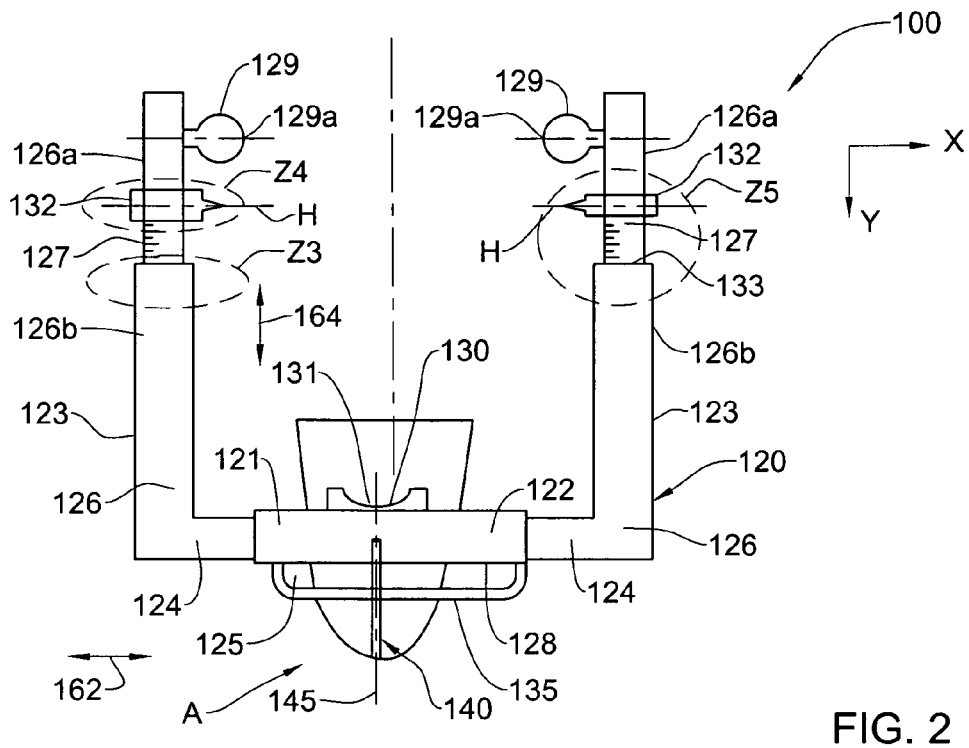
FIG. 2 illustrates in top view a facebow apparatus according to embodiments of the invention.
Figure 3:
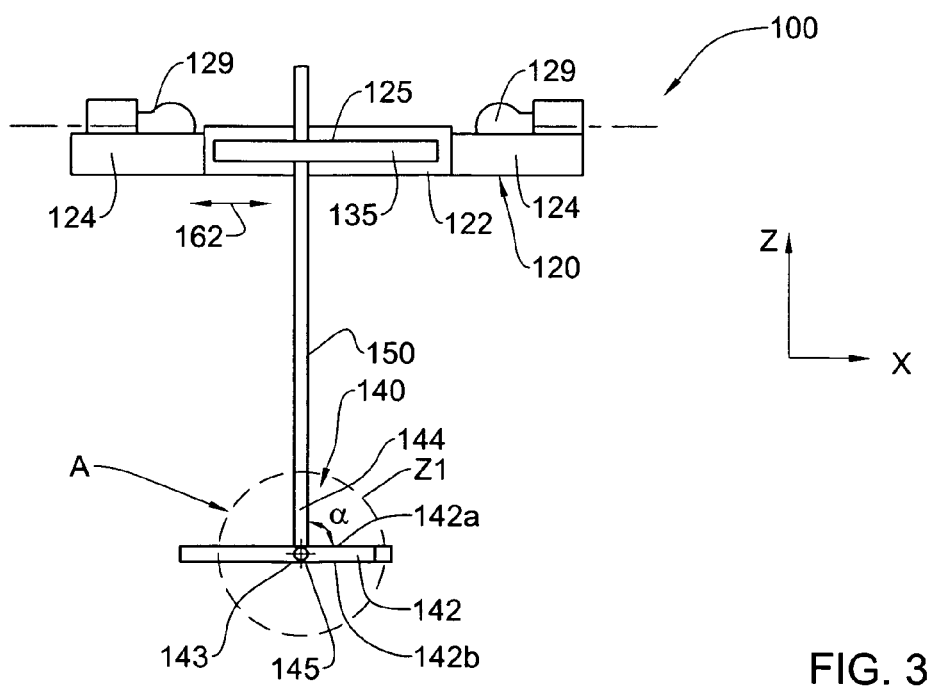
FIG. 3 illustrates in front view the embodiments of FIG. 2.
Figure 4:
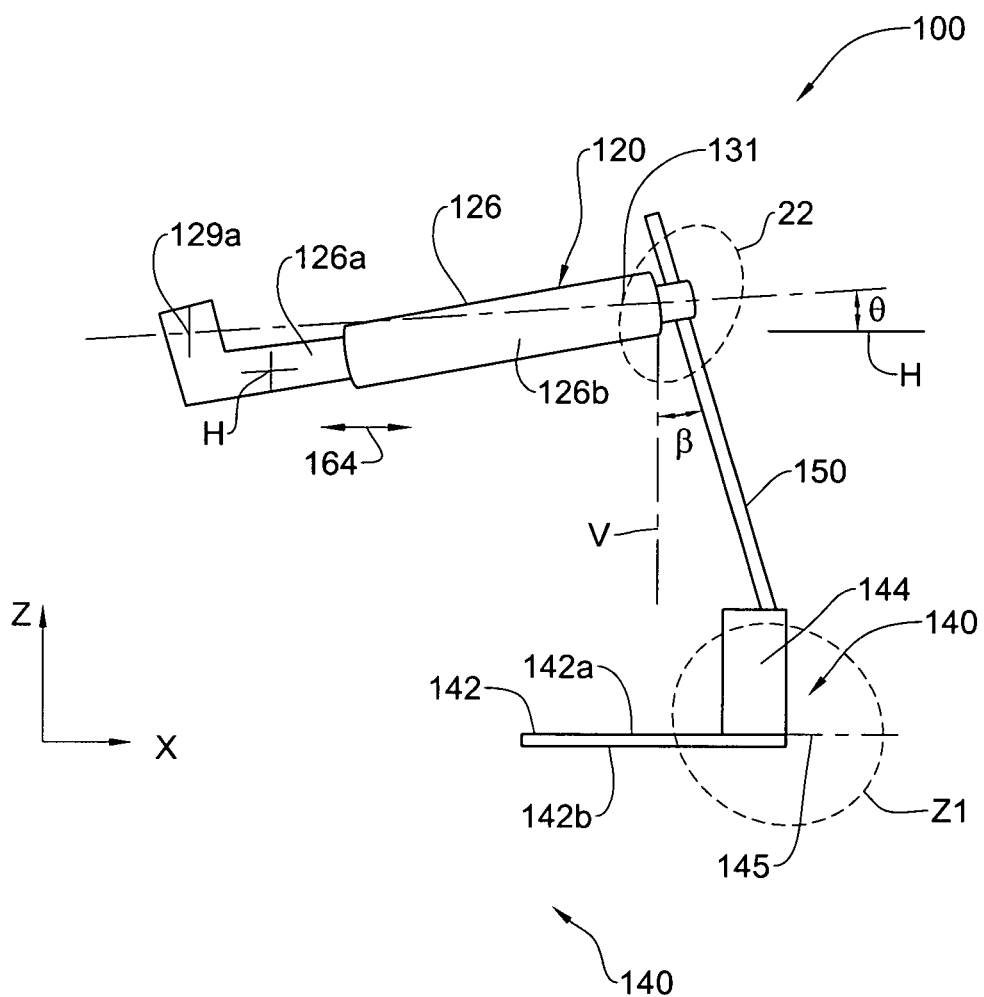
FIG. 4 illustrates in side view the embodiments of FIG. 2.

The facebow apparatus is configured for providing sufficient spatial information for defining the position of the dental arches of a patient in three-dimensions with respect to the hinge axis of the patient's jaw. Referring to FIGS. 2 to 4, a facebow apparatus according to a first embodiment of the invention, which is per se novel, is generally designated with reference numeral 100, and comprises a facebow portion 120 and a bite fork portion 140.

The facebow portion 120 is in the form of a U-shaped member adjustable in two, generally orthogonal directions, enabling this component to be fitted to a range of patients having widely differing anatomies.

The facebow portion 120 comprises a pair of L-shaped arms 123, each comprising a first member 124 joined to a second member 126 at an angle thereto, typically orthogonal, though in alternative embodiments may be acute or obtuse, the first member 124 being telescopically movable with respect to a common central member 122 in a controllable manner enabling the two first members 124 to be reversibly fixed at any desired relative disposition with respect to the central member 122, along directions indicated by the arrows 162. In alternative variations of this embodiment, the two first members 124 may be mechanically coupled, for example via a rack and pinion arrangement (not shown), comprising a pinion gear rotatably mounted inside said central member 122, and the two first members 124 each comprising a rack that is meshed at diametrically opposed sides of the pinion gear, enabling simultaneous and synchronized extension/retraction movements of the two first members 124 with respect to the central member 122.

Each of the respective second members 126 extends in a general rearwards manner from central member 122, and is telescopically adjustable, comprising an inner member 126a controllably reciprocable with respect to outer member 126b to allow length adjustment in the directions marked 164, and reversibly fixable with respect thereto. At or close to a free end of each of the inner members 126a there is an ear canal insertion portion 129 for engagement to the ear canals of a patient.

A scale 127 is marked or printed on the inner member 126a, enabling the relative dispositions between the inner member 126a and outer member 126b of each of the arms 126 to be determined. For example, the scale 127 may be marked to give the displacement of the center 129a of the ear canal insertion portions 129 from the rear portion 121 of the central member 122 in an orthogonal direction therefrom generally along the second member 126. In alternative variations of this embodiments, landmarks, symbols or surface features may be provided on the inner member 126a which are individually visually recognizable and the location of which with respect to the corresponding inner member 126a and in particular portion 129, is known.

Each second members 126, in particular the respective inner member 126a, further comprises a pointer 132 controllably slidable along the length thereof, and for reversibly locking at any desired location thereon; for example, the pointer may be magnetically or mechanically fixable to the corresponding inner member 126a. Each pointer 132 points in an inward direction, generally parallel to said ear canal insertion portions 129, and is configured for being brought into registry with the hinge axis or TMJ of the patient's jaw when the portions 129 are engaged with the patient's ears.

The central member 122 comprises a nose interface 130 on rear portion 121, having a concavity configured for abutting against a part of the nose of the patient, for example the bridge. The front portion 128 of the central member 122 comprises a slot 125 defined by a bar 135 spaced from the frontal portion 128 and extending along part or most of the length thereof.

A representative plane P for the facebow portion 120 may be defined by the three points including the centers 129a of the two portions 129 and a particular point 131 on the nose portion 150.

The bite fork portion 140 comprises a bite plate 142 having a lower surface 142b, and further having an upper surface 142a which in use abuts against the cusp tips of the maxillary arch, or at a least a portion thereof, and a vertical plate 144 that is hingedly mounted to the bite plate 142 at hinge 143 to allow the orientation therebetween to be varied about hinge axis 145. Vertical plate 144 is in use generally aligned with the midsagittal plane of the patient, or alternatively with another sagittal plane of the patient, and hinge axis 145 is substantially aligned with the vertical plate 144 such as to enable the bite plate 142 to be angled at angle α to the vertical plate 144.

A connecting bar 150 coplanarly aligned with the vertical plate 144 extends therefrom in a direction generally away from the bite plate 142, and in use is received in said slot 125. The spacing between the rod 135 and the front face 128 of slot 125 is sufficiently wide to enable the connecting bar 150 to extend an angle β with the frontal plane of the patient. Optionally (not shown) a suitable securing arrangement may be provided for reversibly securing the connecting bar 150 with respect to the slot 125 in a particular spatial relationship.

Referring again to FIG. 5, process 400 broadly includes the following steps:

Step 410—providing a first virtual model 500 representative of at least a portion of the intra-oral cavity of a patient, such as a dental structure, for example.

Step 430—providing a second virtual model 600, representative of at least one geometric structure coupled to the portion of the intra-oral cavity, in particular at least a part of the dental structure, said geometric structure defining at least one spatial parameter of interest associated with a dental procedure, or alternatively, said at least one spatial parameter of interest may be determined by means of the geometric structure.

Step 450—determining a spatial disposition of the first virtual model with respect to the second virtual model.

Step 470—generating, from this spatial disposition, data representative of a spatial relationship between said first virtual model and said at least one spatial parameter of interest.

The data generated in step 470 can then be used in a desired dental procedure 480 for which it may be useful.

In the first embodiment of the invention, data is provided relating to the spatial relationship between a maxillary arch, or a part thereof, and the hinge axis H of the jaw of a patient, which data may then used for constructing physical models of the tooth arches that engage with a dental articulator in a spatial relationship with the articulator hinge axis that parallels the corresponding relationship in the patient.

Step 410 comprises acquiring an accurate 3D representation, (herein also referred to interchangeably as "three-dimensional model", "3D model", "virtual model" and the like)

of the required part of the intraoral cavity of the patient, for example dental structures, which forms the focus of a particular dental procedure for a particular patient and regarding which it is desired to obtain the 3D topographical or surface data thereof. The required part may include may include dental structures such as one or more teeth, or partial or the full mandibular or maxillary arches, or both arches, and/or include details of the spatial relationship between the two arches in occlusion.

In any case, this first virtual model may be provided by scanning the intra-oral cavity in-vivo using any suitable equipment for scanning a patient's teeth. Such scanning equipment may include any suitable optical scanner, for example, the scanner 250 of system 200, or a similar scanner that is not part of the system 200, or a different type of scanner. Alternatively, the first virtual model 500 may be obtained from a physical model of the teeth of the particular patient that was previously prepared. For example, the surfaces of the physical model may be scanned, or the surfaces of the impression from which the model was scanned may be scanned to obtain the virtual model thereof. Alternatively, a composite positive-negative model may be manufactured and processed to obtain 3D digitized data, for example as disclosed in U.S. Pat. No. 6,099,314, assigned to the present Assignee, and the contents of which are incorporated herein in their entirety. Alternatively, the 3D digitized data may be obtained in any other suitable manner, including other suitable intra oral scanning techniques, based on optical methods, direct contact methods or any other means, applied directly to the patient's dentition or to a physical model thereof. Alternatively, X-ray based, CT based, MRI based, or any other type of scanning of the patient or of a positive and/or negative physical model of the intra-oral cavity may be used.

In step 430, the second virtual model 600 is obtained, using system 200, as follows.

Referring to FIG. 5(*a*), in step 431, the bite fork portion 140 is engaged with at least the upper dental arch of the patient—in practice, the patient can clamp the surfaces 142*a* and 142*b* of the bite plate 142 between the upper and lower dental arches. The practitioner then rotates the vertical plate 144 and rod 150 about axis 145, so that they are aligned with the midsagittal plane, or at least such that the vertical plate 140 is co-planar with therewith, but possibly spaced therefrom, while the upper surface 142*a* is abutted against the cusp tips of the upper teeth. This defines an angle α between the plane defining the cusp tips of the upper arch and the vertical plane.

In step 433, the facebow portion 120 is mounted onto the patient by engaging the ear canal insertion portions 129 in the respective ear canals of the patient, and resting the nose interface 130 on a position on the patient's nose such as to ensure that the pointers 132 are aligned with the position of the jaw hinge axis H. This position is previously marked on the skin of the patient by the practitioner in a manner, as is well known in the art. If necessary, the lateral spacings between the arms 123 along direction 162, and/or the spacing between the portions 129 and the central portion 122 along direction 164, may be adjusted as necessary to account for the particular anatomy of the patient and to orient the facebow portion 120 in the required manner, i.e., constrained by the location of the ear canals and of the hinge axis of the patient, and the plane P of the facebow portion 120 is typically inclined at an angle θ to the horizontal plane H.

The rod 150 is received within the slot 125 and fixed in place with respect thereto, the rod still being maintained aligned with the midsagittal plane or at least a sagittal plane.

The various components of the facebow apparatus 100 are secured with respect to one another in the positions provided in the earlier steps so that the facebow apparatus may be considered as a rigid body, at least while step 434 is in progress. Further, the facebow apparatus 100 is mechanically coupled with the intra-oral cavity and with respect to the hinge axis H of the jaw.

In step 434, the scanner 250 is used to scan a number of portions of the facebow apparatus 100 in situ with respect to the part of the dentition, i.e., the dental structure, it is coupled with, as follows, referring to FIG. 5(*b*) and FIGS. 2 to 4.

Step 434*a*—a first zone Z1 is scanned including at least a part of the bite plate 142, vertical plate 144 and at least a portion of the maxillary teeth that are in contact with surface 142*a*. The first zone Z1 scan is at least sufficient to ensure that enough of the bite fork portion 140 may be reconstructed in a portion 602 of the second virtual model from the scan, so that a virtual vertical plane corresponding to the vertical plate 144, and a virtual cusp tip surface corresponding to the upper surface 142*a* can be defined to a preset accuracy. At least some of the dental surfaces in contact with the bite plate, in particular dental surfaces comprised in the maxillary arch are also scanned together with the bite fork, so that the second virtual model includes a virtual portion corresponding to these dental surfaces in contact with the bite plate.

Step 434*b*—a second zone Z2 is scanned including at least a part of the rod 150 and its intersection with the slot 125. The second zone Z2 scan is at least sufficient to ensure that enough of the rod 150 and central member 122 may be reconstructed in a portion 604 of the second virtual model, so that the position and orientation of a virtual entity corresponding to the rod 150 with respect to the central member 122 can be defined to a preset accuracy. The position of rod 150 with respect to the central member 122, in particular the rod 135, and angle β along the sagittal plane with respect to which the rod 150 is nominally aligned, between the rod 150 and the vertical plane V in turn enables the location in 3D of the bite fork apparatus 140 to be defined with respect to the central member 122, and thus to the facebow portion 120.

Step 434*c*—a third zone Z3 is scanned including a part of at least one, and preferably each of the arms 123, including in each case a part of the respective inner member 126*a* that is in visibly adjacent the respective outer member 126*b*. The scan is at least sufficient to ensure that enough of the inner member 123*a* and the respective outer member 123*b* may be reconstructed in a portion 606 of the second virtual model, so that the relative disposition therebetween of a virtual entity corresponding to the respective arm 123 can be defined to a preset accuracy. This enables the relative location of the respective portion 129 to the central member 122 in the virtual model to be determined, and in turn enables the location in 3D of the bite fork portion 140 to be defined with respect to the ear canal engagement portions 129. In alternative variations of this embodiment, in which the facebow portion 120 is non-adjustable, step 434*c* may be omitted. In yet other alternative variations of the invention, it may be possible to simply read off the scale 127, and input this data to enable the relative location of the respective portion 129 to the central member 122 to be determined.

Step 434*d*—a fourth zone Z4 is scanned including a part of at least one, and preferably each of the arms 123, including in each case at least a part of the respective pointer 132 and a part of the respective inner member 126*a* that is in visibly adjacent the pointer 132. The fourth zone Z4 scan is at least sufficient to ensure that enough of the inner member 123*a* and the respective pointer 132 may be reconstructed in a portion 608 of the second virtual model, so that the relative disposition therebetween of a virtual entity corresponding to the pointer and its position on the respective arm 123 can be defined to a preset accuracy. This enables the relative location of the pointer 132 with respect to the facebow portion 120 in the virtual model to be determined, and in turn enables the location in 3D of the bite fork apparatus 140 to be defined with respect to the jaw hinge axis. In alternative variations of this embodiment, step 434d may be omitted.

In steps 434c and 434d, the scale 127 may provide useful clues for determining the relative positions of the portion 129 and of the pointer 132 with respect to the facebow portion 120 in the virtual model.

Optionally, steps 434c and 434d may be combined so that a zone Z5 is scanned including the pointer 132 and, contiguously therewith, the intersection 133 between the inner member 126a and 126b as viewed from outside the apparatus 100. This enables the position of the pointer 132 relative to the intersection 133, and thus with respect to the bite fork portion 140 and so on to be determined, and thus enable portions 606 and 608 of the second virtual model 600 to be reconstructed together.

The preset accuracy required in each step may depend on the specific dental procedure regarding which the generated data is to be applied later.

The virtual model 600 may be completed by combining the portions 602, 604, 606 and 608 in their relative special positions. This may be done in a number of ways. For example, a third virtual model of the facebow apparatus 100 may be provided within the computer environment of the computer system 260, the third virtual model being manipulable to enable the relative dispositions and movements of the movable components in the real facebow apparatus 100 to be simulated. Thus, the third virtual model is effectively a combination of "component" virtual models, each corresponding to a respective one of the various components of the physical facebow apparatus 100. Each of the portions 602, 604, 606 and 608 is registered or otherwise matched with respect to the corresponding part of the third virtual model, by manipulating the component virtual models thereof, such that each aforesaid portion is in registry with the corresponding part of the third virtual model. The third virtual model is thus effectively manipulated in a manner to simulate the relative dispositions of the components in the physical model of the facebow apparatus, and the second virtual model 600 is then generated by effectively adding the dental surface reconstructed on the bite plate, as provided in step 434a.

Alternatively, it is sufficient to spatially combine the portions 602, 604, 606 and 608 within the computer environment in their respective correct relative positions, and this provides the second virtual model 600. To do so, each portion is manipulated so as to conform to a common, global coordinate system, and this may be done by identifying particular landmarks or features in each portion, determining the corresponding position of such landmarks in a nominal virtual model of the facebow apparatus, and applying a corresponding transformation to the particular portion to conform to the same coordinate system as in the aforesaid nominal virtual model. Such features may correspond to features in the physical facebow including, for example, the intersection 133, the front face 128, the attachment point between the bar 150 and the vertical plate 144, and so on.

Thus, in step 430, the structure in the form of the facebow apparatus 100 is mechanically coupled to the dental structure. In alternative variations of this embodiment it may only be necessary to spatially couple any suitable geometrical structure to the dental structure in a fixed spatial relation that is determinable from a virtual model of the coupled structures via scanning thereof, the geometrical structure being such that its spatial relationship to a body reference, for example basic reference planes or axes of the head of the patient, is also concurrently known or determinable, enabling the spatial relation of the dental structures to the aforesaid body reference such as basic reference planes or axes to be determined from the scanning. Thus, according to an aspect of the invention there is provided a method for providing a spatial relationship of the dental structure of a patient with respect to the desired body reference of the patient, comprising:

(A) generating a virtual model representative of at least a part of said dental structure coupled with the geometric structure in a first spatial relationship therewith, wherein a second spatial relationship between said geometric structure and said body reference is known or determinable; and (B) determining the spatial relationship between said part of said dental structure and said body reference from said first spatial relationship and said second spatial relationship.

Thus, step (A) is analogous to step 430, including steps 431 and 433, for example, and step (B) is analogous to step 434, modified as necessary according to the specific type of geometrical structure that is coupled to the dental structure, mutatis mutandis.

In step 450 the spatial disposition of the first virtual model with respect to the second virtual model is determined by registering the virtual model of the dental surfaces obtained in step 434a with the first virtual model. Such registration is conducted in the computer environment of computer system 260 by manipulating one or another or both of the first virtual model 500 and the second virtual model 600 so that the virtual dental model surfaces in the second virtual model, obtained via step 434a, coincide with a corresponding part of the first virtual model. As the dental surfaces are rigid structures, and assuming that there have been no changes in the dentition between steps 410 and 430, the virtual dental surfaces in both virtual models should be matchable to a high degree of accuracy. Once matched, the spatial relationship of the bite plate 142, and thus of the vertical plate 144 and the sagittal plane thereof, the spatial relationship of the hinge axis as determined by pointers 132, and so on, with respect to the first virtual model 500 are automatically determined.

In alternative variations of this embodiment, step 410 may be omitted. For example, in step 430 the dental structure may be sufficiently defined by the scanning of the coupled dental structure/geometric structure for the purposes of the user. Thus step 450 may also be omitted. To separate the surface data corresponding to the dental structure from the surface data corresponding to the geometrical structure that is scanned in situ with the dental structure, if this is desired, may be accomplished by registering a virtual model of the part of the geometrical structure that is coupled to the dental structure with a virtual model of this geometrical structure (obtained independently of the scan at step 430), or by identifying and distinguishing surface data corresponding to the dental structure from the surface data corresponding to the geometrical structure.

In step 470, any suitable desired data relating to spatial disposition of the first virtual model to the second virtual model can be generated, this data being representative of a spatial relationship between the first virtual model and said at least one spatial parameter of interest. In one particular application of the embodiment, the parameter of interest is the hinge axis H of the jaw of the patient, and the aforesaid data relates to the disposition of the first virtual model 500 relative to the virtual representation of the hinge axis, HA.

The data generated in step 470 can then be used in a desired dental procedure 480 for which it may be useful. Such a procedure 480 may be the construction of a physical articulation model of the teeth of the patient, and the relative disposition of the first virtual model 500 to the virtual hinge axis HA may be used to enable a physical model of the teeth to be mounted onto a particular articulator such that they are positioned therein in six degrees of freedom in a spatial relationship with the articulator hinge axis in a manner simulating that generated in step 470 for the virtual model.

For example, the first virtual model may be further manipulated to include an alignment arrangement, for example as disclosed in U.S. Pat. No. 7,220,124 to the present Assignee, and the contents of which are incorporated herein in their entirety.

A physical model may be manufactured from the first virtual model—for example via a material removing process such as CNC or via any other suitable process, for example rapid prototyping, the physical model comprising a physical representation of the alignment arrangement, which enables the physical model of the teeth to be mounted directly to the respective dental articulator in the correct spatial orientation with respect to the articulator hinge axis, and in proper occlusion arrangement.

Figure 6:
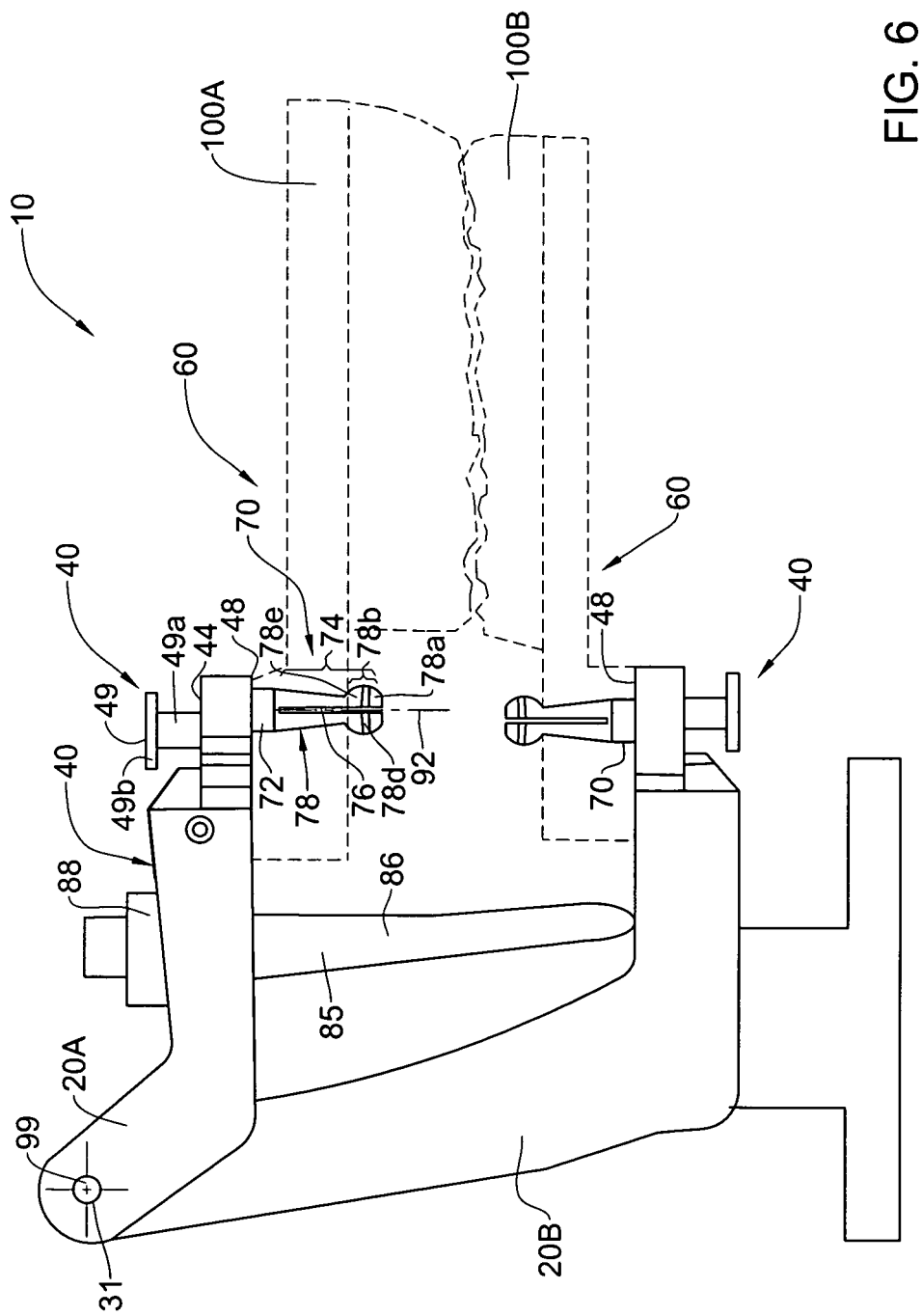
FIG. 6 illustrates in side view a dental articulator apparatus according to an embodiment of the invention.
Figure 7:
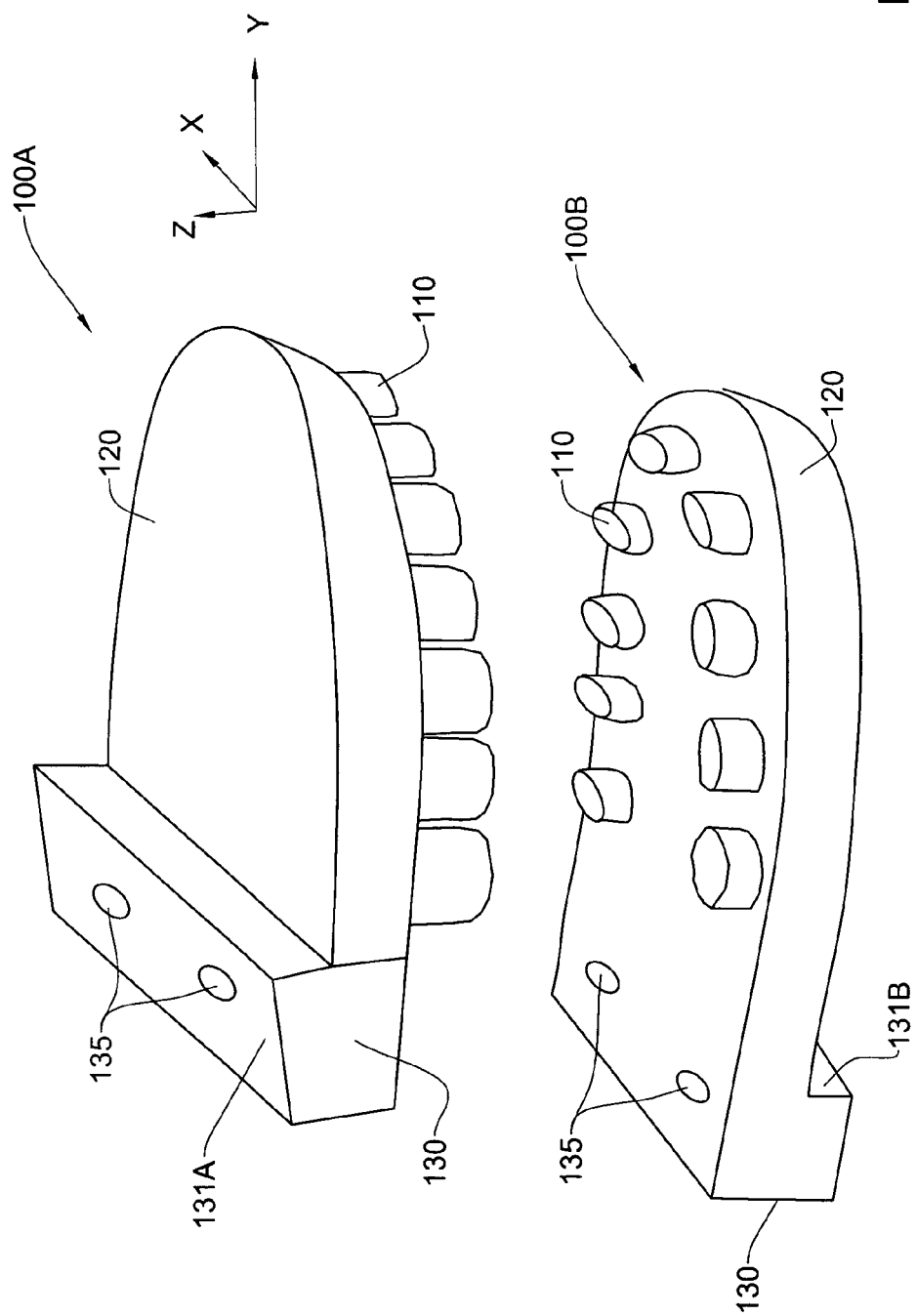
FIG. 7 illustrates examples of dental models designed and manufactured for use with the embodiment of FIG. 6 or FIG. 10.

Referring to FIGS. 6 and 7, an embodiment of such an articulator, designated herein with reference numeral 10, comprises an upper arm 20A and a lower arm 20B hingedly joined together with respect to pivot axis 99 at hinge arrangement 31, each arm comprising a mounting bracket 40 formed therewith, comprising a model mounting arrangement 60.

The model mounting arrangement 60 is configured for enabling a dental model of part or of the full respective dental arch (upper or lower) to be mounted thereonto. In the illustrated embodiment, such mounting is reversible, but in alternative embodiments of the invention the model mounting arrangement may permanently mount the dental models to the corresponding arms 20A, 20B. Thus, in alternative embodiments of the invention, the details of the mounting arrangement 60 may vary according to the particular geometry of the dental model, in particular the engagement arrangement thereof, if any.

The articulator 10 according to the illustrated embodiment is configured for use with physical dental models 100A, 100B, each of which may comprise a positive teeth representation of one or more teeth 110, formed on a respective base 120, and further comprising a respective mounting block 130 formed at one end of the corresponding model 100A, 100B that is in closest proximity to the relative position of the axis H of the real jaw. In this embodiment, each mounting block 130 is formed with an abutment surface 131A, 131B, respectively, and comprises an alignment arrangement comprising a pair of laterally-spaced (or otherwise spaced) cylindrical apertures 135.

In the illustrated embodiment, the mounting arrangement 60 comprises a pair of transversely spaced, substantially parallel engagement prongs 70 that are configured for reversibly engaging with respect to the apertures 135 of the corresponding tooth model 100, and an abutment surface 48 of the respective arm. The positions and orientations of the prongs 70 and abutment surfaces 48 of each arm 20A, 20B, in relation to the hinge axis 99, are known for the particular articulator. The pair of apertures 135 are longitudinally and laterally located on the corresponding models 100A, 100B in a particular manner with respect to the teeth representations 110, and furthermore the abutment surfaces 131A and 131B are each inclined with respect to the occlusal plane, so as to provide the desired spatial relationship between the models 100A, 100B and their occlusal plane with respect to the axis 99 when mounted to the articulator 10.

Thus, the tooth models can be designed in a virtual manner starting with the aforesaid first virtual model, and then adding to this model, in a virtual sense (i.e., within the computer environment of computer system 260 or another computer system), virtual representations of the mounting blocks 130, the particular geometry of each mounting block being designed such as to displace and/or rotate the first virtual model in up to six degrees of freedom so that the cusp tip plane thereof is in the correct relationship to the hinge axis AH when mounted to a geometry as defined by the arms, hinge and mounting arrangement 60 of the particular articulator 10.

The teeth representations 110 may include representations of the teeth of part or the full dental arch, and may optionally contain one or more representations of one or more dental preparations in place of corresponding teeth, the preparations being for the purpose of fitting dental prostheses thereto.

Each prong 70 comprises a cylindrical base 72 projecting from abutment surface 48, and a resilient portion 74 projecting from the base 72. The resilient portion 74 comprises a plurality of elongate resilient elements 78 cantilevered with respect to the base 72 in circumferential arrangement and circumferentially spaced via longitudinal gaps 76. The elements 78 each comprises a sloping portion 78a that radially slopes towards the longitudinal axis 92 of the prong 70, and an enlarged portion 78b at the free end of the prong 70 that radially projects further outwardly than the perimeter of base 72 when the elements 78 are in the datum, unstressed condition. The enlarged portion 78b comprises a conical or rounded free end, a convex waist portion 78d defining the radially outermost surfaces of enlarged portions, and an engaging shoulder adjacent the sloping portion 78a. Thus, together the plurality of elements 78 form a substantially frustoconical or pyramidal portion comprising the sloping portions 78a, and a bulging portion (comprising the enlarged portions 78b) having a rounded free end.

The external width or diameter of the base 72 is just less than the internal width or diameter of the apertures 135, and the elements 78 and gaps 76 are configured for enabling the elements 78 to be radially elastically deflected inwardly, such that the radially outermost surfaces of enlarged portions 78b, i.e. defining waist 78d, are displaced from axis 92 to a distance from the centerline 92 of the elements 78 substantially equal to the radius of the apertures 135.

The longitudinal length of the prong 70 is greater than the depth of aperture 135, and the latter is substantially similar to the sum of the longitudinal length of the base 72 together with the longitudinal length of the sloping portions 78a taken along axis 92. In other embodiments, though, the apertures 135 may be diverging or stepped, for example, or otherwise configured, for enabling the prongs 70 to be anchored within the corresponding apertures 135 via the restoring force generated onto the aperture walls by the elements 78.

To engage a tooth model to the corresponding bracket 40, the respective mounting block 130 is brought into proximity with the respective arm 20A or 20B such that the prongs 70 are aligned with the apertures 135 of the respective model 100A or 100B. The mounting block 130 is then pushed towards the abutment surface 48 so that the prongs 70 are received into the apertures 135. In doing so, the corresponding elements 78 of the prongs 70 are elastically deformed, so as to enable the enlarged portions 78b to pass through the aperture 135, this being facilitated via the rounded free ends 78c. When the block 130 is in abutment with abutment surface 48, the enlarged portions 78a fully clear the apertures 135 and spring back to the unstressed state, or closer thereto, and engage against an outer surface of the block 130 around the mouth of apertures 135, locking the block 130, and thus the tooth model 100A or 100B, in place.

In variations of this embodiment, more than two prongs may be provided, mutatis mutandis, the tooth models 100A, 100B being correspondingly configured for being engaged thereto. In yet other variations of this embodiment, a single prong may be provided, mutatis mutandis, and this may optionally be further configured for preventing relative rotation between the corresponding tooth model and the bracket 40 about the longitudinal axis 92 of the prong, for example comprising a suitable circumferential stop arrangement or a non-axisymmetric cross-section.

To disengage the tooth model 100 from the mounting bracket 40, the block 130 may be pulled away from the abutment surface 48. In doing so, the elements 78 must be deformed inwardly, and this may be done manually or by means of a tool, for example pliers. Alternatively, the shoulders 78e may be suitably sloped or rounded, and/or the mouth of the apertures 135 may also be suitable sloped or rounded, so that as the block 130 is pulled away the elements 78 are automatically pushed inwardly in the radial direction.

To further facilitate disengagement, a quick release probe 49 may be provided inn each arm 20. The probe 49 comprises a pushing element (not shown) at the end of a shaft 49a that is reciprocally mounted freely to the mounting bracket 40 in a direction substantially parallel to axis 92, and located generally inbetween the prongs 70. A knob 49b is provided at the projecting end of the shaft 49a. The pushing element is normally accommodated in a recess (not shown) in the abutment surface 48, so as to enable the pushing element to be flush therewith when in the inactive condition. When it is desired to disengage the tooth model 100, the probe 49 is actuated by pushing the same towards the bracket 40, and the pushing element forces the block 130 away from the bracket 40. Once the enlarged portions 78b have been deformed and are accommodated in the apertures 135, the model may be fully removed from the bracket 40 with relative ease.

Optionally, a pivot stop 85 may be provided, configured for limiting the relative rotation of the arms 20A, 20B towards each other such to prevent the teeth models 100A and 100B being pressed against each other with undue force or beyond the occlusal plane. Stop 85 comprises a generally rigid strut 86 connected to arm 20A and projecting towards the second arm 20B. Strut 86 essentially abuts against a surface of arm 20B when the articulator is in the occlusal position, which allows the teeth models (not shown in this figure) to touch at the occlusal plane, but prevents further rotation of the arms 20A, 20B towards one another, while permitting rotation away from one another. Optionally, the strut 86 may be adjustable via a screw 88, which enables the strut to be displaced further towards or away from the lower arm 20B to define a different stop position.

The arms 20A, 20B may be made from or comprise any suitable materials or combination of materials, for example metals (including, for example, aluminium, stainless steel, brass, titanium, and so on), plastics (including for example flexible plastics and/or hard plastics), wood, composites, ceramics, and so on.

In an alternative variation of this embodiment, the teeth models are designed virtually, and subsequently manufactured, for example via CNC machining/milling methods, other material removal methods, or by rapid prototyping methods, each tooth model integrally with articulator arms and a part of a hinge arrangement, so that the two tooth models can be hingedly attached to one another at the hinge arrangement. The integral arms are virtually attached to the first virtual model of the dentition to provide the hinge axis thereof to be provided at the correct spatial relationship to the models, as determined by the scanning of the facebow apparatus. For example, and referring to FIG. 9, such as integral articulated physical model may be manufactured as two separate components from two standard blanks, 501, 502, which are then hingedly mounted to one another at hinge axis 510. The first blank 501, representing the upper arch of the patient, is formed with an articulation arm 503 (including integral hinge part 510a) and integral machinable block 505, which is then milled or otherwise machined via CNC instructions to produce a physical model of the upper arch of the patient (or part thereof) at the correct position and orientation with respect to axis 510, simulating the real arch of the patient and its relative orientation and position with axis H of the patient. The second blank 502, representing the lower arch of the patient, is formed with an articulation arm 504 (including integral hinge part 510b) and integral machinable block 506, which is then milled or otherwise machined via CNC instructions to produce a physical model of the lower arch of the patient (or part thereof) at the correct position and orientation with respect to axis 510, simulating the real arch of the patient and its relative orientation and position with axis H of the patient. The two machined models 501 and 502 can then be mounted together at the hinge parts 510a, 510b, to mutually align the hinge axis 510. The shape and form of the arms 503, 504 may be standard, for example, at least for a range of patient attributes such as age, sex, ethnic group, and so on, while the size and position of the respective blocks, 505, 506, are such to allow any reasonable tooth or arch geometry to be machined therefrom.

Figure 10:
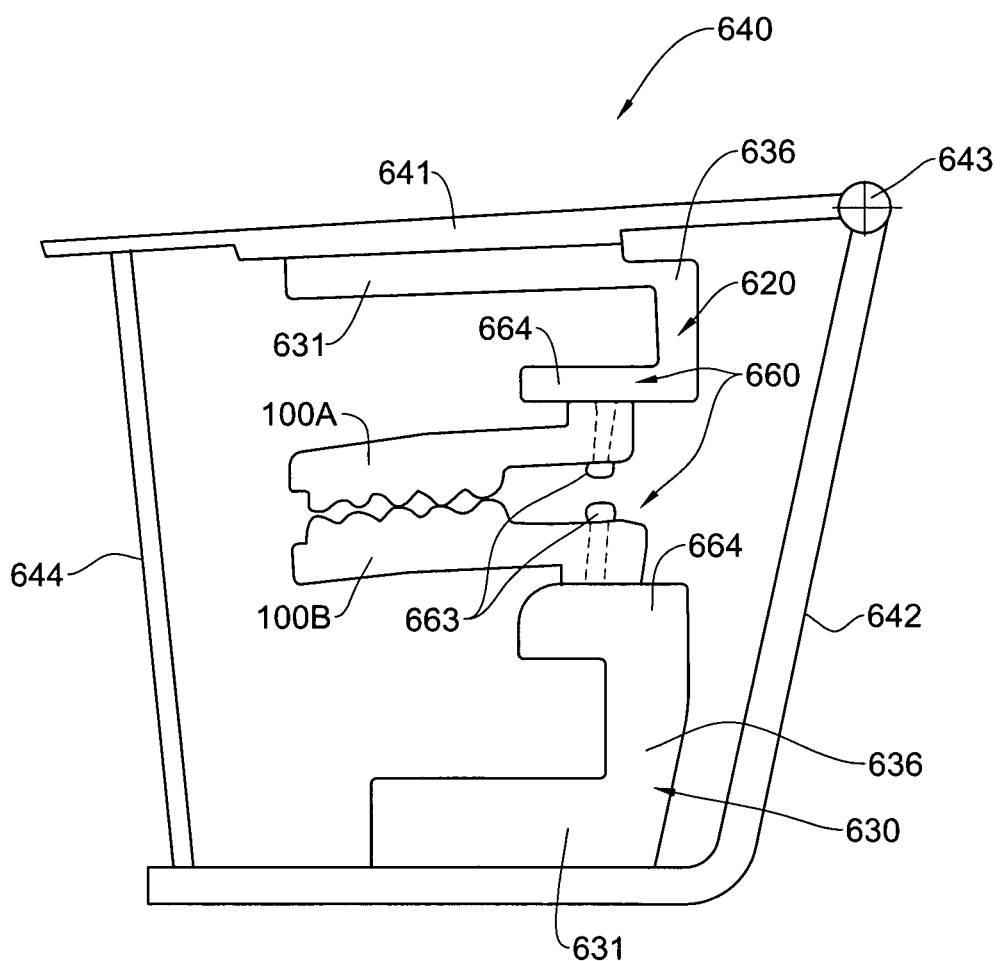
FIG. 10 illustrates in side view a dental articulator apparatus according to another embodiment of the invention.

Another embodiment of an articulator arrangement according to the invention is illustrated in FIG. 10, comprising a basic articulator 640 and adaptors 620, 630. Basic articulator 640 represents an articulator onto which a plaster model may be mounted according to the prior art, for example any suitable standard articulator currently marked under many different well-known brand names. Alternatively, the articulator 640 may comprise any other suitable dental articulator. In any case, the articulator 640 comprises arms 641, 642 hingedly mounted together at hinge axis 643, and may comprise a stop 644 mounted to arm 641 and configured for limiting rotational movement between the arms in a direction towards one another. Adaptors 620, 630 are mounted to the upper arm 641 and lower arm 642, respectively, of the articulator 640, and are configured for enabling tooth models 100A, 100B of the upper and lower jaws, respectively, as disclosed herein with respect to FIG. 7, for example, to be mounted to the articulator 640 in the correct spatial relationship with respect to the hinge axis 643. Each adaptor 620, 630 comprises a base part 631, a model mounting arrangement 664, and spacer portion 636.

The base part 631 is configured for mounting the adaptor 620 or 630 to the respective arm 641 or 642 in a known and fixed spatial relationship. The model mounting arrangement 664 similar to model mounting arrangement 60 disclosed for the embodiment of FIG. 6, mutatis mutandis, and configured for enabling a respective dental model 100A, or 100B of part or of the full respective dental arch (upper or lower) to be mounted thereonto, and comprise engagement prongs 663 and abutment surface 667 similar to engagement prongs 70 and abutment surface 48, respectively, of the embodiment of FIG. 6, mutatis mutandis. Spacer portions 636 rigidly interconnect the respective base part 631 to the respective model mounting arrangement 664 such as to provide a known spatial relationship between the axis 643 on the one hand, and prongs 663 and abutment surface 667 on the other hand, in order that the respective models 100A and 100B may be designed and manufactured in a manner such that the mounting blocks 131A, 131B can engage with the respective mounting arrangement 664 to provide the required spatial relationship between the tooth models and the axis 643, in six degrees of freedom, for the particular articulator 640.

For any particular articulator design, a number of sets of adaptors 630, 640 may be provided, each set providing a different spatial relationship between axis 643, and prongs 663 and abutment surface 667, to enable accommodation of dental models of patients having widely varying anatomies to be used with the same articulator. For example, two sets of adaptors may be provided for use with an articulator 640—one set for use with models of adult teeth, and the other for use with models of children's teeth. When designing models 100A, 100B for use with a particular articulator 640, the designer may design the models assuming that one set of adaptors is to be used thereof. If the resulting virtual models are unsatisfactory, for example from a mechanical integrity point of view, the models may be designed again, using a different set of adaptors, and the process repeated until an acceptable combination of adaptors and teeth model is obtained. Optionally, such an iterative process may be carried out automatically, once the virtual model of the teeth has been established.

In alternative variations of these embodiments, any other suitable facebow apparatus may be used for engaging to a patient in the respective normal manner, and this may be followed by scanning portions of the facebow apparatus as necessary to obtain a second virtual model wherein the positions of the parameter of interest, including the jaw hinge axis and the midsagittal plane, and to enable a reconstruction of at least a portion of the teeth that is coupled (also referred to interchangeably herein as "optically coupled" or "visually coupled") with an identifiable part of the dental surfaces of the patient. This enables steps 450 and 470 to be carried out in a similar manner to that disclosed above regarding the facebow apparatus 100, mutatis mutandis.

Figure 15:
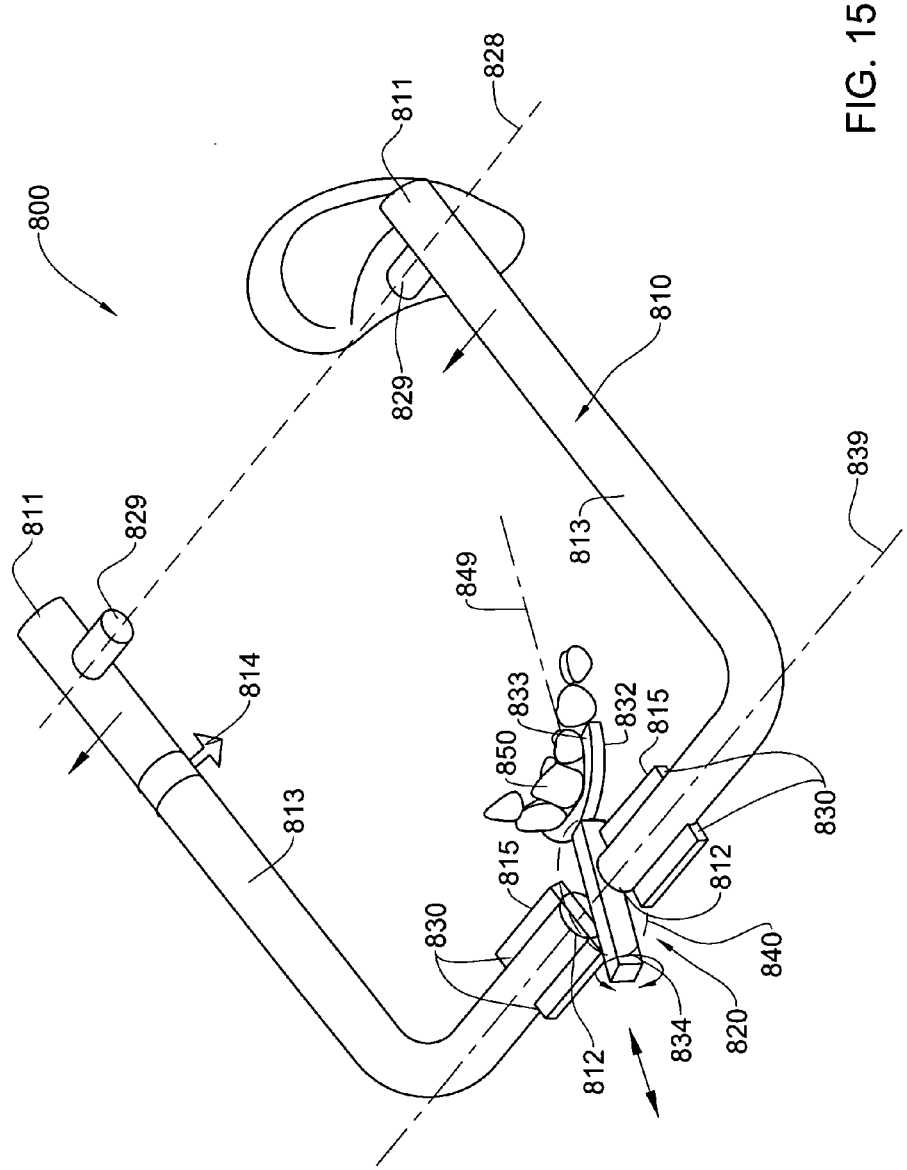
FIG. 15 illustrates in isometric view a facebow apparatus according to another embodiment of the invention.
Figure 16:
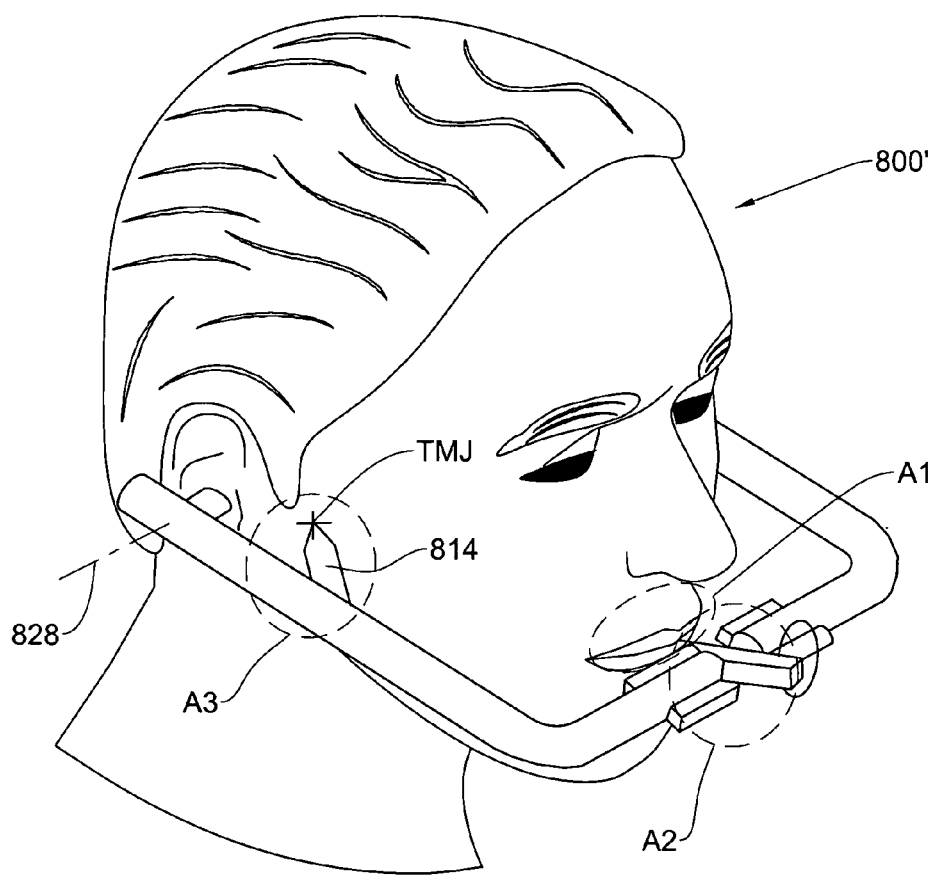
FIG. 16 illustrates embodiment of FIG. 15, engaged with respect to a patient.
Figure 17:
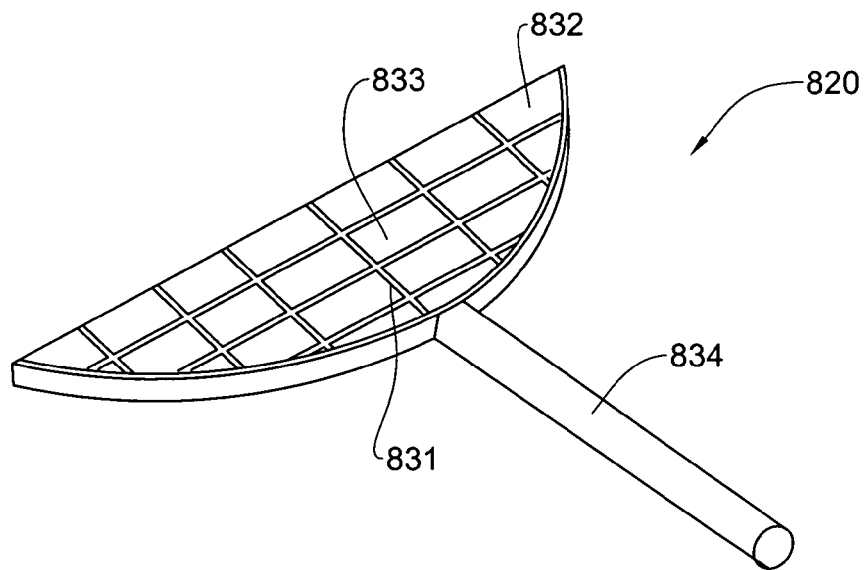
FIG. 17 illustrates a bite fork portion of the embodiment of FIG. 15.

One such alternative variation of the first embodiment is illustrated in FIGS. 15, 16, and 17 and is designated with the reference numeral 800. The facebow apparatus 800 comprises a U-shaped facebow portion 810, and a bite fork portion 820, substantially similar to facebow portion 120 and bite fork portion 140 of the first embodiment, mutatis mutandis, with the following differences. In the embodiment of FIGS. 15 and 16, the facebow portion 810 comprises a pair of L-shaped arms 813, each having an ear canal insertion portion 829 at or close to a free end 811 thereof for engagement to the ear canals of a patient. The ear canal insertion portions 829 define an axis 828 through the ear canals of the patient when they are engaged therein. The other ends 812 of arms 813 are pivotably connected together about axis 839 at coupling 840 (shown as a dotted line), onto which bite fork portion 820 is coupled, providing the bite fork portion 820 with at least three degrees of freedom with respect to the facebow portion 810. Axis 839 is generally perpendicular to a sagittal plane of the patient. The first to degree of freedom is rotation of the bite fork portion 820 with respect to the facebow portion 810 about axis 839.

Facebow portion 810 also comprises near ends 812 planar portions 830 which have a characteristic planar surface 815 of a particular plan shape—for example a rectangle as illustrated- and the position and orientation of the planar portions 830 with respect to the ear canal insertion portions 829 is known.

Bite fork portion 820 comprises a bite plate 832 having an upper surface 833 which in use abuts against the cusp tips of the dental structure 850 of the maxillary arch of the patient, or at a least a portion thereof, and a support arm 834 at a distal end thereof rigidly attached to the bite plate 832. The support arm 834 is slidingly received in the coupling 840 along axis 849 (substantially orthogonal to axis 839), and the relative position of the arm 834, and thus of the bite fork portion 820, with respect to the coupling 840 may be selectively adjusted. Furthermore, the arm 834 is configured for being selectively rotated with respect to the coupling 840 about axis 849. Thus, the second and third degrees of freedom are rotation and translation of the bite fork portion 820 with respect to the facebow portion 810 about and along axis 849, respectively.

Each arm 813 further optionally comprises a pointer 814 controllably slidable along the length thereof, and for reversibly locking at any desired location thereon, and the pointer can be manipulated to be brought into registry with the hinge axis or TMJ of the patient's jaw when the portions 829 are engaged with the patient's ears.

All the dimensions of the apparatus 800 are known (and thus the relative spatial disposition between the coupling 840 and the facebow portion 810, and in particular the ear canal insertion portions 829 is thus fixed), except for the relative spatial disposition between the bite fork portion 820 and the facebow portion 810, since relative movement between the two is permitted via the coupling, and their relative spatial disposition is fixed in a manner essentially determined by the anatomy of the patient.

In use, the apparatus 800 is mounted to the patient as follows. The facebow portion 810 is mounted onto the patient by engaging the ear canal insertion portions 829 in the respective ear canals of the patient. Then, the bite fork portion 820 is engaged with at least the upper dental arch of the patient—in practice, the bite plate 832 is abutted against at least the upper dental arch, by rotating the bite fork portion 820 about axis 839 and/or 849 and/or by translating the bite fork portion 820 along axis 849 as required for such abutment. Of course, the facebow portion 810 may be tilted with respect to the ear canals as required to enable the engagement of the bite fork portion with the dental structure 850. Optionally, the pointers 814 may be aligned with the position of the jaw hinge axis H or TMJ, and this position may have been previously marked on the skin of the patient by the practitioner in a manner, as is well known in the art, for example.

Figure 18:
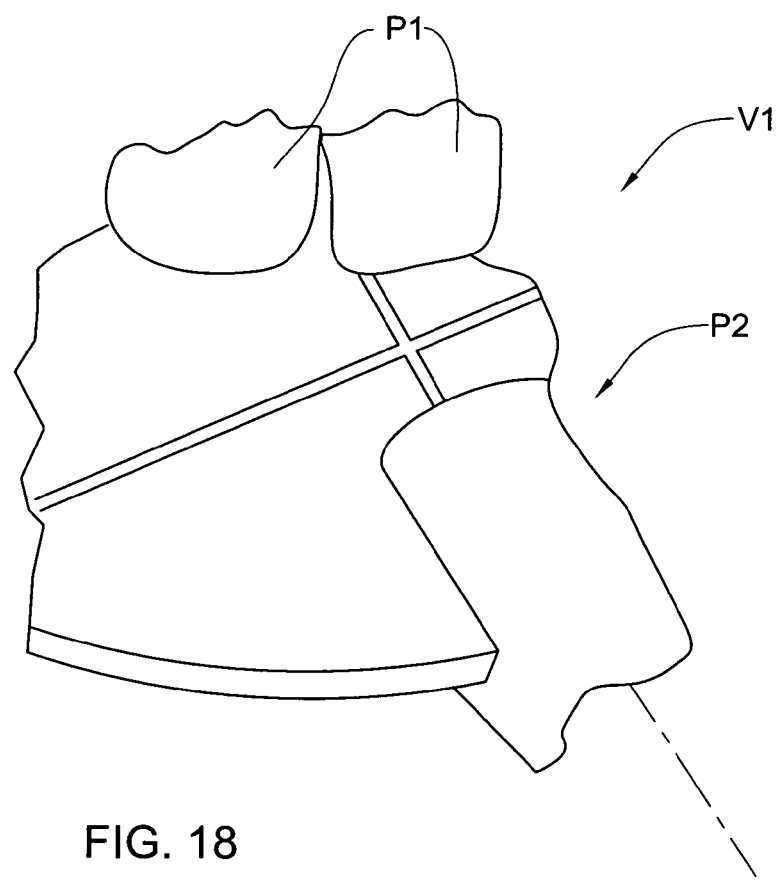
FIG. 18 illustrates a virtual model of a dental structure coupled with bite fork portion of the embodiment of FIG. 15.

With the position and orientation of the bite fork portion 820 fixed with respect to the facebow portion 810, and this spatial orientation may be locked via a suitable clamp member (not shown), the following steps are conducted, referring to FIG. 16. Zone A1 is scanned using scanner 250, including part of the dentition 850 coupled with the bite plate 832, and a virtual model V1 is generated of the scanned zone A1, for example as illustrated in FIG. 18. This virtual model V1 comprises one part P1 that is representative of the dental structure 850, and another part P2 that is representative of the bite fork portion 820.

A second zone A2 is scanned, including the coupling 840 and at least part of the facebow portion 810 and part of the bite fork portion 820 in the vicinity of the coupling 840 to provide another virtual model V2 which shows the position and orientation between the coupling 840 and the facebow portion 810, and the position and orientation between the coupling 840 and the arm 834.

Since the geometry of the bite fork portion 820 is known, it is then possible to refer both virtual models V1 and V2 to the same coordinate system. Part P2 can be analysed so that the position and orientation of P1 with respect to P2, and thus to the facebow portion 810 can be determined. Since the relative position of the ear canal insertion portions 829 with respect to the facebow portion 810 is also known, thus the position and orientation of P1 with respect to axis 828 through the ear canals can be determined.

A virtual model of the patient's dentition including the dental structure 850 can then be registered with respect to P1, and thus the position and orientation of the axis 829, which is a body reference of interest, can be determined with respect to the virtual model of the patient's dentition in a common coordinate system. For example, dental structure 850 may be the cusps of some of the upper teeth of the patient, as observed via the open mouth of the patient, while the aforesaid virtual model of the patient's dentition may be the full upper dental arch that includes these cusps.

Optionally, another scan may be provided of a zone A3 including the markers 814, such that the position and orientation of the markers with respect to the arms 813 may be determined, and thus the position and orientation of the TMJ, which is also a body reference of interest, can be determined with respect to the virtual model of the patient's dentition in a common coordinate system.

Referring to FIG. 17, the bite plate 832 may optionally comprise indicia or other markings, for example a series of intersecting lines 831 engraved therein, protruding therefrom or marked thereon, which are easily identifiable in the virtual model V1 and thus assist in identifying the relative spatial position between P1 and P2, as well as facilitating the step of combining the virtual models V1 and V2 to the same coordinate system.

Figure 19:
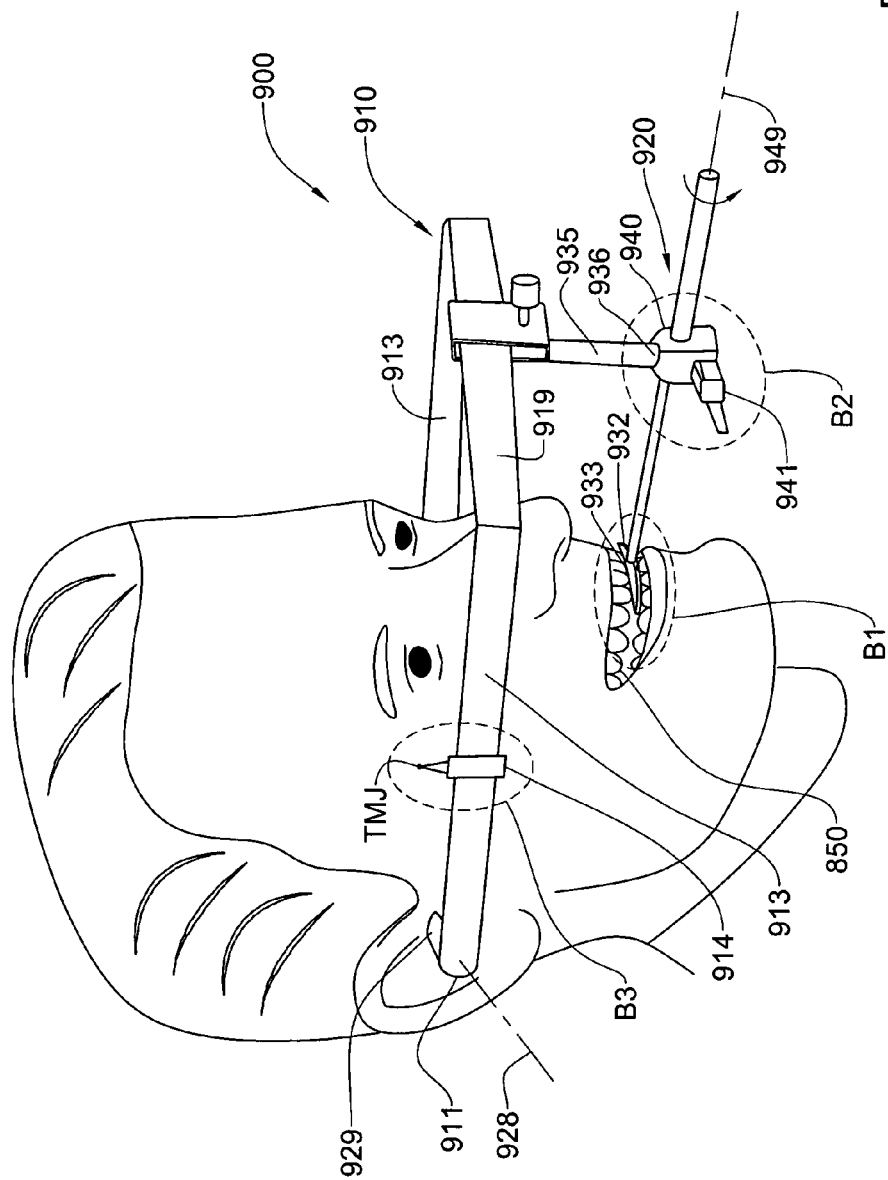
FIG. 19 illustrates in isometric view a facebow apparatus according to another embodiment of the invention.

Another alternative variation of the first embodiment is illustrated in FIG. 19 and is designated with the reference numeral 900. The geometric structure is in the form of facebow apparatus 900, which comprises a U-shaped facebow portion 910, and a bite fork portion 920, substantially similar to facebow portion and bite fork portion of the first embodiment and variations thereof, mutatis mutandis, with the following differences. In the embodiment of FIG. 18, the facebow portion 910 comprises a pair of arms 913 joined to a base 919 to form a U, each arm 913 having an ear canal insertion portion 929 at or close to a free end 911 thereof for engagement to the ear canals of a patient. The ear canal insertion portions 929 define an axis 928 through the ear canals of the patient when they are engaged therein.

A downwardly depending arm 935 is centrally connected to the base 919, and comprises at its lower end 936 a coupling 940 onto which bite fork portion 920 is coupled, providing the bite fork portion 920 with at least two degrees of freedom with respect to the facebow portion 910.

All the dimensions of the apparatus 900 are known (and thus the relative spatial disposition between the coupling 940 and the facebow portion 910, and in particular the ear canal insertion portions 929 is thus fixed), except for the relative spatial disposition between the bite fork portion 920 and the facebow portion 910, since relative movement between the two is permitted via the coupling, and their relative spatial disposition is fixed in a manner essentially determined by the anatomy of the patient.

Bite fork portion 920 is similar to the bite fork portion 820 of the embodiment of FIGS. 15 to 18, mutatis mutandis, and comprises a bite plate 932 having an upper surface 933 which in use abuts against the cusp tips of the dental structure 850 of the maxillary arch of the patient, or at a least a portion thereof, and a support arm 934 at a distal end thereof rigidly attached to the bite plate 932. The support arm 934 is slidingly received in the coupling 940 along axis 949 (substantially along the midsagittal plane or a sagittal plane of the patient), and the relative position of the arm 934, and thus of the bite fork portion 920, with respect to the coupling 940 may be selectively adjusted. Furthermore, the arm 934 is configured for being selectively rotated with respect to the coupling 940 about axis 949. Thus, the aforesaid at least two degrees of freedom include rotation and translation of the bite fork portion 920 with respect to the facebow portion 910 about and along axis 949, respectively.

Each arm 913 further optionally comprises a pointer 914 controllably slidable along the length thereof, and for reversibly locking at any desired location thereon, and the pointer can be manipulated to be brought into registry with the hinge axis or TMJ of the patient's jaw when the portions 929 are engaged with the patient's ears.

In use, the apparatus 900 is mounted to the patient as follows. The facebow portion 910 is mounted onto the patient by engaging the ear canal insertion portions 929 in the respective ear canals of the patient. Then, the bite fork portion 920 is engaged with at least the upper dental arch of the patient—in practice, the bite plate 932 is abutted against at least the upper dental arch, by rotating the bite fork portion 920 about axis 949 and/or by translating the bite fork portion 920 along axis 949 with respect to coupling 940 as required for such abutment. Of course, the facebow portion 910 (including the whole apparatus 900) may be tilted with respect to the ear canals as required to enable the engagement of the bite fork portion with the dental structure 850. Optionally, the pointers 914 may be aligned with the position of the jaw hinge axis H or TMJ, and this position may have been previously marked on the skin of the patient by the practitioner in a manner, as is well known in the art, for example.

With the position and orientation of the bite fork portion 920 fixed with respect to the facebow portion 910, and this spatial orientation may be locked via clamp member 941, the following steps are conducted. Zone B1 is scanned using scanner 250, including part of the dentition 850 coupled with the bite plate 932, and a virtual model V1' is generated of the scanned zone B1. This virtual model V1' comprises one part P1' that is representative of the dental structure 850, and another part P2' that is representative of the bite fork portion 920.

A second zone B2 is scanned, including the coupling 940 and part of the bite fork portion 920 in the vicinity of the coupling 940 to provide another virtual model V2' which enables the position and orientation between the arm 934 (and thus the bite fork portion 920) and coupling 940 (and thus the facebow portion 910) to be determined.

Since the geometry of the bite fork portion 920 is known, it is then possible to refer both virtual models V1' and V2' to the same coordinate system, as with other variations of this embodiment. Part P2' can be analysed so that the position and orientation of P1' with respect to P2', and thus to the facebow portion 910 can be determined, since the geometry of the arm 935, coupling 940, base 919 and arms 913 is also known. Since the relative position of the ear canal insertion portions 929 with respect to the facebow portion 910 is also known, thus the position and orientation of P1' with respect to axis 929 through the ear canals can be determined.

A virtual model of the patient's dentition including the dental structure 850 can then be registered with respect to P1', and thus the position and orientation of the axis 929, which is a body reference of interest, can be determined with respect to the virtual model of the patient's dentition in a common coordinate system. For example, dental structure 850 may be the cusps of some of the upper teeth of the patient, as observed via the open mouth of the patient, while the aforesaid virtual model of the patient's dentition may be the full upper dental arch that includes these cusps.

Optionally, another scan may be provided of a zone B3 including the markers 914, such that the position and orientation of the markers with respect to the arms 913 may be determined, and thus the position and orientation of the TMJ, which is also a body reference of interest, can be determined with respect to the virtual model of the patient's dentition in a common coordinate system.

As with bite plate 832, mutatis mutandis, bite plate 932 may also have indicia or other markings, to assist in identifying the relative spatial position between P1' and P2', as well as facilitating the step of combining the virtual models V1' and V2' to the same coordinate system.

Regarding the embodiments of FIGS. 2 to 4, 15 to 19, scans of zones of the respective apparatus that are not coupled with the respective dental structure may be performed while the respective apparatus is engaged with the patient, or after the removal of the respective apparatus from the patient—for example, regarding the embodiment of FIG. 19, zones B2 and B3 can be made with the apparatus engaged or disengaged from the patient. However, the scan of the zone including the coupling between the tooth structure and apparatus, for example zone B for the embodiment of FIG. 19, must be done while the respective apparatus is engaged with the patient.

Nevertheless, the above embodiments may be utilized in a slightly varied manner to enable a virtual model representative of the coupling between the dental structure and the apparatus to be obtained after the apparatus is disengaged from the patient.

Figure 20:
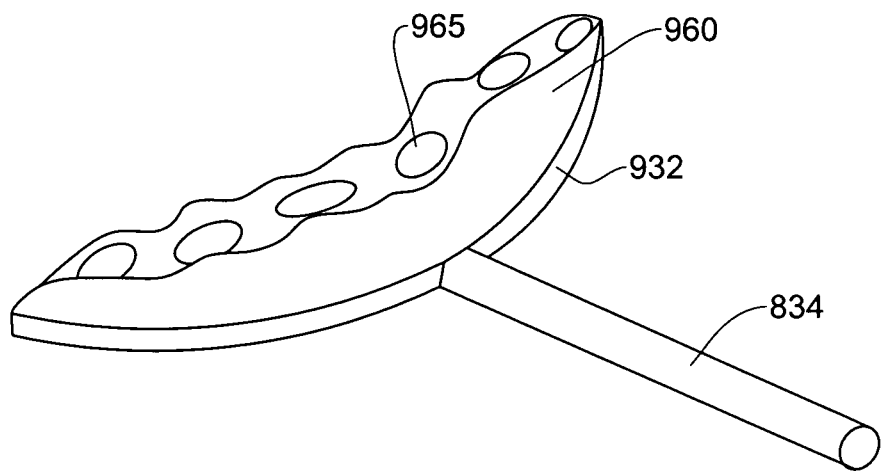
FIG. 20 illustrates a bite fork portion of a variation of the embodiment of FIG. 19.

Referring to FIG. 20, with respect to the embodiment of FIG. 19, the bite plate 932 comprises a layer of impressionable material 960. Such a material may be include materials routinely used in the art to obtain physical impressions of the dentition, and which are subsequently used in the art to cast therefrom stone or plaster models of the dentition, for example. In use, the patient abuts the bite plate 932 to the dental structure 850, and in doing so creates an impression 965 in the material 960, corresponding to the contours and shape of the dental structure 850. Of course, the remainder of the apparatus 900 is properly engaged to the patient, as described above, mutatis mutandis. Once the material 960 has set, the apparatus may be disengaged and removed from the patient, including the bite plate and material. Now, a scan of the bite plate 932 coupled to the impression 965 can be taken, and this will enable a virtual model to be generated, in which the position and orientation of dental structure with respect to the bite plate 932 can be determined, since the part of the virtual model corresponding to the impression 965 corresponds to the dental structure, and in fact a virtual model of the whole dentition may be registered with the virtual model corresponding to the impression 965. Thus, the virtual model of the dentition may be spatially related to a desired body reference such as axis 928 or the TMJ as disclosed above, mutatis mutandis.

In a similar manner to the embodiment of FIG. 19, the embodiments of FIGS. 2 to 4, 15 to 18 may be modified to include a layer of impression material and used in a similar manner, mutatis mutandis.

In a second embodiment of the invention, and referring again to FIGS. 2 to 4, the bite fork portion 140 is provided as a separate and independent tool that may be coupled to the oral cavity of the patient and scanned together therewith, in a similar manner as disclosed herein for the first embodiment of the facebow apparatus 100, mutatis mutandis, without the need to provide or use the full facebow apparatus 100, mutatis mutandis. Step 410 is as for the first embodiment, mutatis mutandis, and in step 430, according to the second embodiment, the spatial parameter of interest is the position and orientation of the plane of the cusp tips with respect to the midsagittal plane, or at least with respect to a sagittal plane, and this may be accomplished in a similar manner to determining the position of a vertical plane associated with the vertical plate 144, in a similar manner to that disclosed above for the first embodiment, mutatis mutandis. Alternatively, the spatial parameter of interest may simply be the generally orientation of the teeth with respect to the midsagittal plane, or at least with respect to a sagittal plane. In any case, in step 450 according to the second embodiment, the first virtual model of the intraoral cavity that has already been obtained is then matched to the dental surfaces scanned while coupled to the bite plate 142, and in step 470 according to the second embodiment, the spatial position and orientation of the sagittal or midsagittal plane with respect to the first virtual model is determined, being aligned with or at least parallel to the vertical plate. In turn, this information, i.e., the spatial position and orientation of the sagittal or midsagittal plane with respect to the first virtual model, is determined, and may be useful in planning, inter alia, a prosthodontic procedure, for example, in which one or more incisor prosthetics, including veneers for the incisors, may be designed to be aligned as close as possible to the sagittal plane, even if the cusp tip plane or the occlusal plane is tilted to the right or the left of the midsagittal plane when the patient is viewed from the front.

In alternative variations of the second embodiment, rather than the bite fork portion 140, any suitable rigid plate, strip, rod, or the like may be aligned with the midsagittal plane of the patient, in close visual proximity to the intraoral cavity, so that a portion of the thus vertical plate is visually coupled to a portion of the teeth during a scanning thereof in step 430, sufficient for enabling reconstruction of the vertical surface of the plate and of enough of the dental surface to allow a match in step 450 with the first virtual model to be achieved.

In yet other variations of this embodiment, any suitable geometrical structure, for example in the form of an artifact, may be coupled to a portion of the teeth during a scanning thereof in step 430, sufficient for enabling reconstruction of the geometrical structure and of enough of the dental structure to allow a match in step 450 with the first virtual model to be achieved. The geometrical structure can comprise any shaped structure the shape of which provides information linking the geometrical structure to the midsagittal plane of the patient directly, or indirectly via any other reference plane or axis of the head of the patient.

Figure 11:
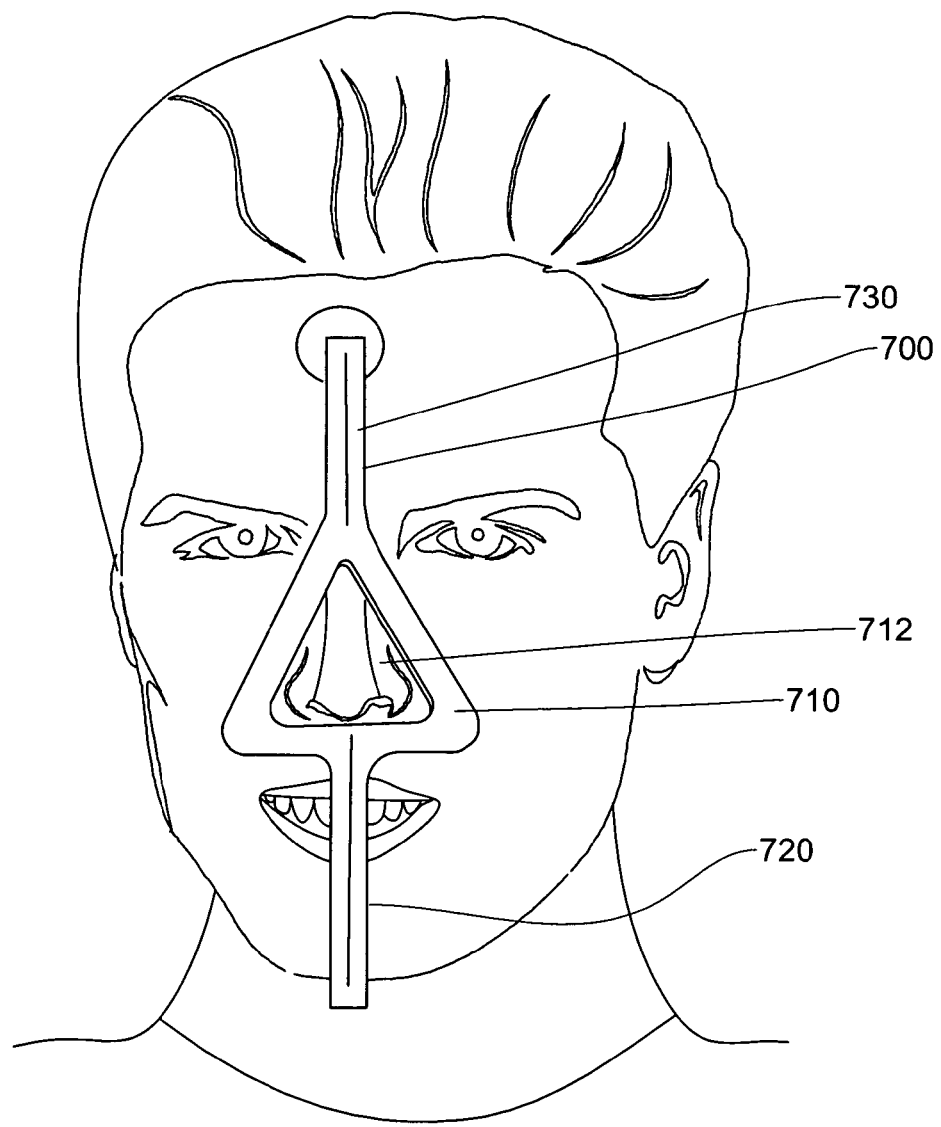
FIG. 11 illustrates a geometrical structure according to an embodiment of the invention in situ on a patient's face.
Figure 12:
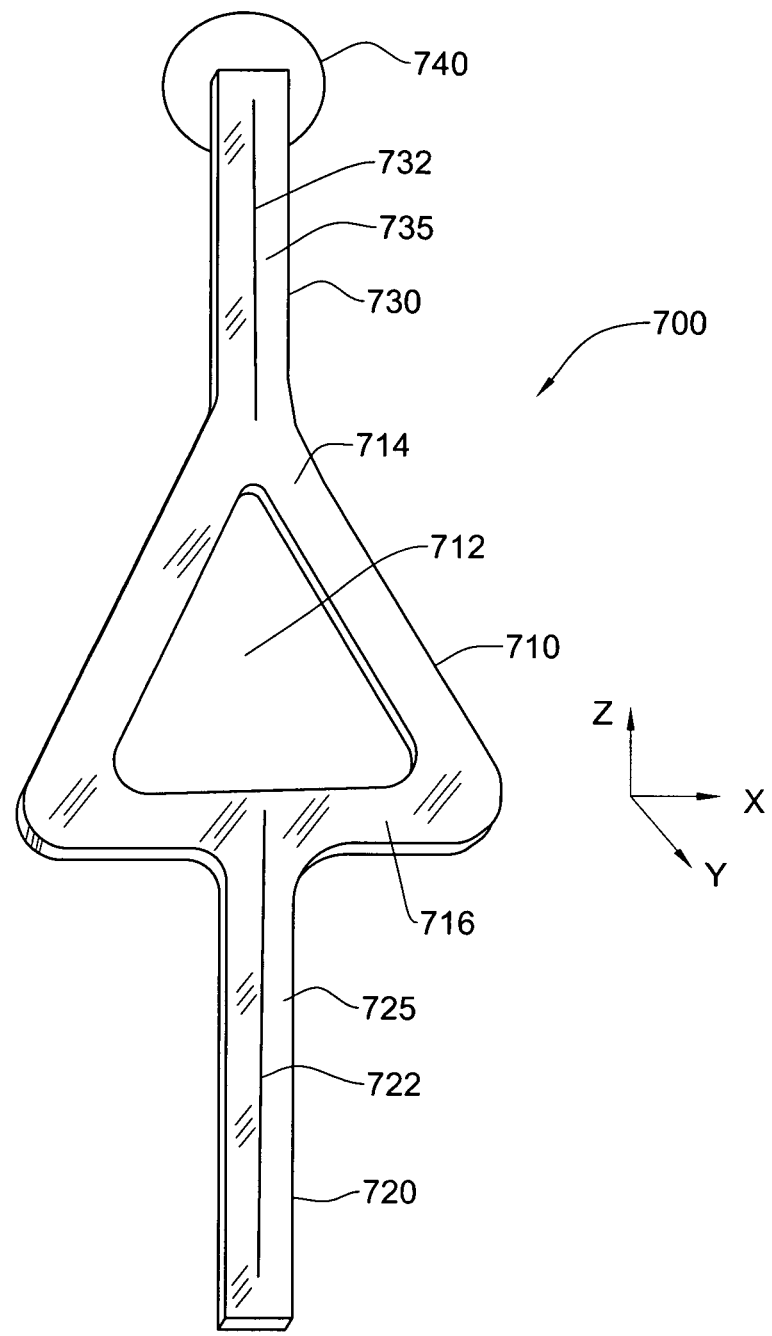
FIG. 12 illustrates the embodiment of FIG. 11 in greater detail.

For example, and referring to FIGS. 11 and 12, another variation of the second embodiment is illustrated, in which such a geometrical structure, designated with the reference numeral 700 comprises a first nose circumscribing portion 710 in the form of a an isosceles triangle-shaped piece of sheet material having a triangular shaped opening 712, the portion 710 having an upper vertex 714 between the two equal sides of the triangle, and lower base portion 716. A lower strip 720 of sheet material is generally coplanar with portion 710 and projects downwardly from the center of the base portion 716, in a direction generally orthogonal thereto. An upper strip 730 of sheet material projects upwardly from the vertex 714, in a direction generally parallel and aligned with respect to the lower strip 720. Each of the strips 720, 730 optionally comprises a marking in the form of lines 722, 732 which provide light intensity and/or colour contrast with the rest of the respective strip. Lines 722 and 732 are in fixed geometrical relationship with the outer surfaces 725, 735 of the respective strips 720, 730, and the lines 722, 732 are aligned and parallel to one another, though in other variations of the embodiment of FIGS. 11 and 12 other markings may be provided, or the lines may be non-aligned and/or non-parallel to one another, or no lines or markings of any kind may be provided.

Portion 710 is thus an interconnecting portion for interconnecting strip 720 and 730.

In any case, in the embodiment of FIGS. 11 and 12, or variations thereof, the strip 720, nose circumscribing portion 710 and strip 730 are in a fixed and known geometrical relationship with respect to one another. In particular, the geometrical structure 700 is formed as an integral piece from sheet material, though in variations of this embodiment it may be made from several pieces joined together in any suitable fashion. In this embodiment, the artifact is substantially rigid and is planar, for example about the Z-Y plane, though in variations thereof the artifact may be non-planar. In yet other variations of this embodiment, the geometrical structure may be semi-rigid, for example allowing reversible bending or controlled deformation about the Z-Y plane, though limited or no bending or deformation being allowed along other planes, for example. In such cases, the positions of the various portions of the geometrical structure 700 are known, knowable or determinable, or alternatively, the various portions of the geometrical structure 700 are at least identifiable.

The opening 712 is configured for enabling the nose of a patient to protrude therefrom while the portion 710, in particular the vertex 714 and/or the base portion 716 are as close as possible to the intraoral cavity and nose bridge, respectively, of the patient.

At least the upper part of strip 730 comprises an adhesive patch 740, or alternatively may comprise an adhesive layer on the back thereof.

The geometrical structure 700 may be used as follows. The artifact 700 is placed over the face of the patient such that the nose passes through opening 712, and the strips 720, 730 are aligned with the midsagittal plane of the patient. In particular, the lines 722, 732 may be aligned with the midsagittal plane. The spacing and alignment between the strips 720, 730 facilitate alignment thereof with respect to the midsagittal plane. Then, the geometrical structure 700 is temporarily affixed to the patient's head in this position by means of the adhesive patch 740, and/or by other means, for example additional adhesive tape, elastic bands, and so on. The patient's mouth should be open at least sufficiently for enabling at least some of the dental surfaces to be viewed in proximity to and visually coupled with the lower strip 720 and/or any other part of the geometrical structure 700. The visible dental surfaces are then scanned together with at least a portion of the lower strip 720 coupled therewith, this lower portion being sufficient to enable therefrom the position of the strip 720 itself, and thus the position of the midsagittal plane. Thus, the lower strip 720 is in close visual proximity to the intraoral cavity, so that a portion of the strip 720, in particular a portion of line 722, is visually coupled to a portion of the teeth during a scanning thereof in step 430, sufficient for enabling reconstruction of the strip 720 and line 722 (and thus of the position of the midsagittal plane), and of enough of the visible dental surface to allow a match in step 450 with the first virtual model to be achieved.

In alternative variations of the embodiment of FIGS. 11 and 12, the nose circumscribing portion may take any other suitable form, including, for example a three-dimensional form such as a cup or the like to fit over the nose of the patient.

Figure 13:
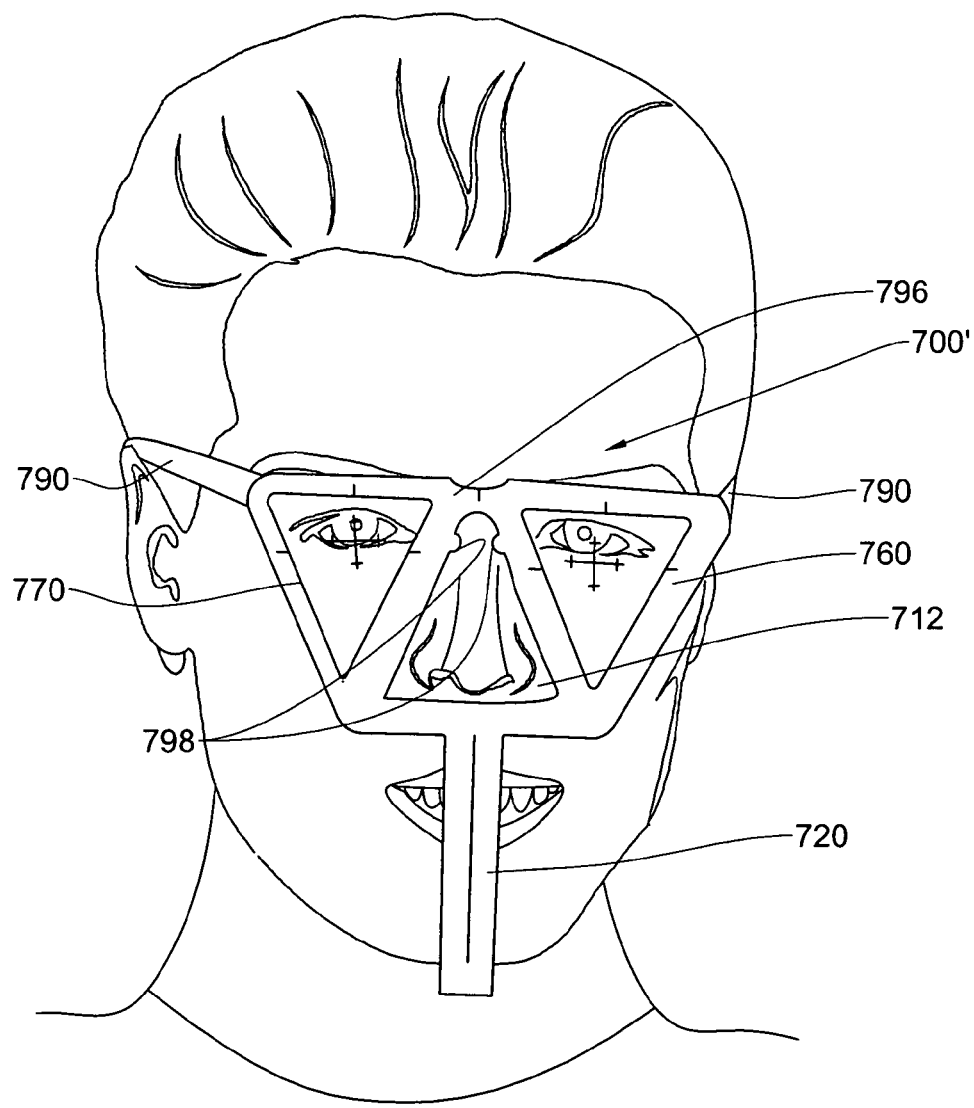
FIG. 13 illustrates a geometrical structure according to another embodiment of the invention in situ on a patient's face.
Figure 14:
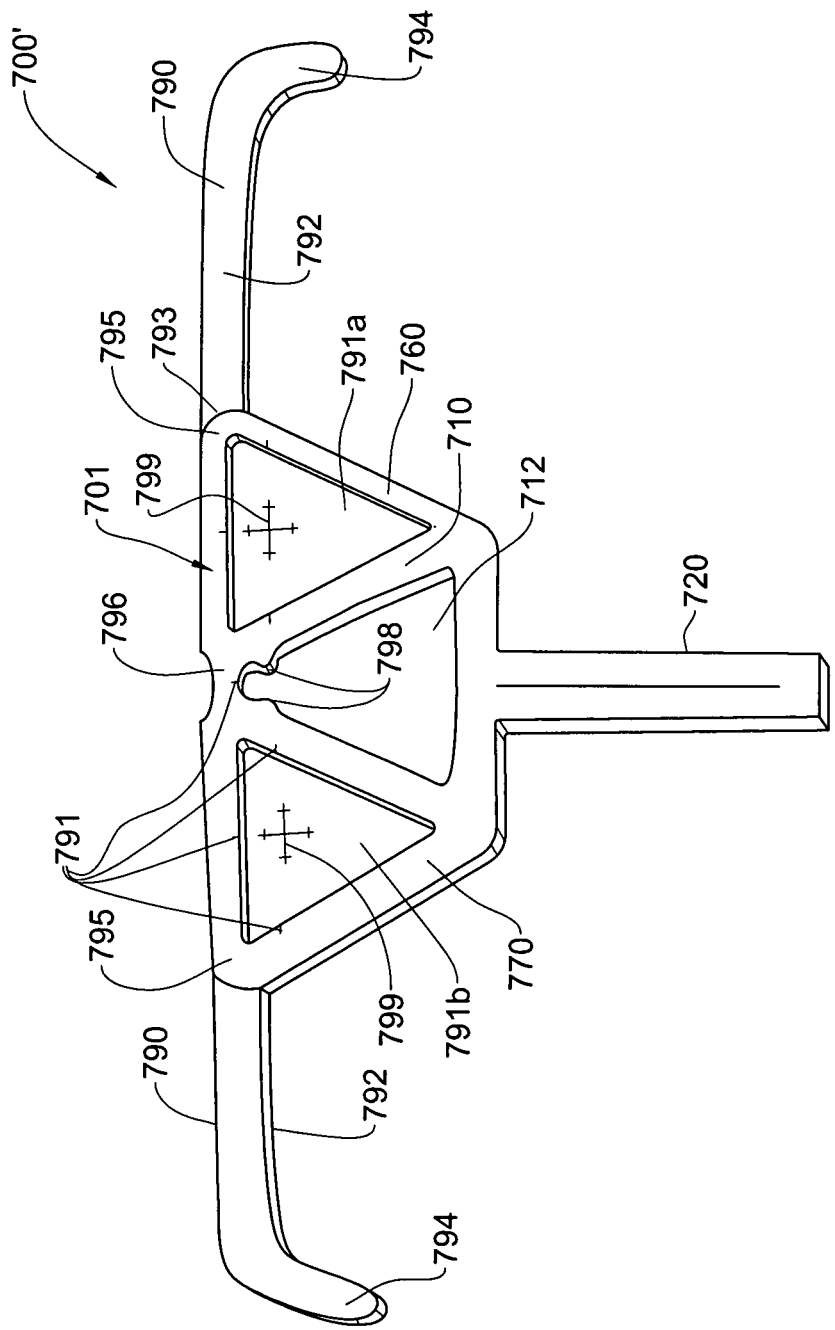
FIG. 14 illustrates the embodiment of FIG. 13 in greater detail.

In one particular variation of the embodiment of FIGS. 11 and 12, illustrated in FIGS. 13 and 14, the geometrical structure, herein designated 700', comprises all the elements and features of the embodiment of FIGS. 11 and 12, and further comprises a left eye encircling portion 760 and a right eye encircling portion 770 that define openings 791a and 791b, respectively, that enable the eyes to be seen therethrough and further facilitates alignment of the strip 720 with the midsagittal plane by centering the portions 760 and 770 over the respective eyes of the patient when the nose is protruding from the opening 712. The portions 760 and 770 thus comprise in this embodiment V-shaped or C-shaped strips of material connected to the portion 710, to form a frame 701, though any other suitable shape that facilitates centering the artifact with respect to the eyes, and thus with respect to the midsagittal plane, may also be used. Optionally, target markings 791 may be provided to facilitate centering of the geometrical structure 700' with respect to the eyes and/or the nose bridge of the patient. In this embodiment, the strip 730 is omitted, though in other variations of the embodiment, an upper strip may be provided. Furthermore, the geometrical structure 700' comprises a pair of side members 790 that act in a similar manner to the temple portions of eyeglasses, and each have a shaft 792 and bend 794 to fit over and rest against the ears of the patient, and the opening 712 comprises a bridge 796 with opposed nosepads 798 for resting over the bridge of the nose. Each shaft 792 is connected to the respective portion 760, 770 via a hinge 793, for example a film hinge, to enable the side members 790 to be pivoted between a flat configuration (for example, manufactured integrally with the rest of the artifact from a sheet of material), a deployed configuration, for installing on a patient, for a folded configuration, for storage. Optionally, the openings 791a, 791b may comprise a transparent film of material, which further optionally may comprise markings 799 thereon to further facilitate centering the portions 760, 770 on the eyes in a symmetrical manner. In alternative variations of the embodiment of FIGS. 13, 14, the side elements 790 may be replaced with a head encircling elastic chord, for example, the ends of which are fixed one each to the respective sides 795 of the frame.

In use, the geometrical structure 700' is placed over the face of the patient such that the nose passes through opening 712, and the bridge 796 sits over the nose bridge of the patient, and the elements 790 rest over the respective ears of the patient, in a similar manner to fitting eyeglass frames on the face, mutatis mutandis. The geometrical structure 700' is manipulated until the eyes of the patient are centralized within the portions 760, 770, and strip 720, in particular line 722, are then nominally automatically aligned with the midsagittal plane of the patient. The geometrical structure 700' may optionally be further affixed to the patient's head in this position by any suitable means, for example adhesive tape, elastic bands, and so on. The patient's mouth should be open at least sufficiently for enabling at least some of the dental surfaces to be viewed in proximity to the lower strip 720 and/or any other part of the geometrical structure 700'. The visible dental surfaces are then scanned together with at least a portion of the lower strip 720, this lower portion being sufficient to enable therefrom the position of the strip 720 itself, and thus the position of the midsagittal plane. Thus, the lower strip 720 is in close visual proximity to the intraoral cavity, so that a portion of the strip 720, in particular a portion of line 722, is visually coupled to a portion of the teeth during a scanning thereof in step 430, sufficient for enabling reconstruction of the strip 720 and line 722, and of enough of the visible dental surface to allow a match in step 450 with the first virtual model to be achieved.

Thus, in the embodiments of FIGS. 11 to 14, the geometrical structure in each case (also referred to herein as an apparatus) comprises a first part that is alignable with a body reference including a reference axis or plane of choice of the patient, for example a midsagittal plane, and a second part that is in proximity to the dental structure of interest such as to be optically coupled thereto when scanned. The first part and the second part are in a fixed or determinable geometric and/or spatial relationship with respect to one another. Thus, the position of the aforesaid body reference, reference axis or reference plane of the patient can be defined with respect to the second part, the spatial relationship between the second part and the dental structure can be determined by scanning the two, so that the disposition of the dental structure with respect to the body reference, reference axis or plane can be determined.

It is to be noted that the embodiments of FIGS. 11 to 14 can be modified, mutatis mutandis, to provide alignment information of the scanned dental surfaces with respect to any other body reference including a reference plane or axis of the patient, by providing the relative disposition of such a body reference, reference plane or axis with respect to the lower strip 720, for example. Furthermore, the strip 720 may be replaced in alternative embodiments with a bar or other suitable physical structure, for example, having a fixed or determinable geometrical/spatial relationship with the upper strip 730 in the case of the embodiment of FIGS. 11, 12, or the frame 701 in the case of the embodiment of FIGS. 13, 14.

Furthermore, the embodiments of FIGS. 11 to 14 may be constructed from a former cut or stamped from sheet material, for example cardboard or plastic sheet material, and may furthermore be made as low-cost items suitable for disposal after one use, or alternatively various uses with a single patient. Alternatively, the embodiments of FIGS. 11 to 14 may be constructed from less inexpensive materials, for example metals, for multiple use, and preferably capable of being sterilized, for example via autoclave, between uses, or between patients.

In yet other variations of this embodiment, the aforesaid geometrical structure is coupled to the dental structure in an exclusively visual manner, such as for example via visual markings on the face of the patient, without the need for an external physical structure to be mounted to the patient visually coupled to the intra oral cavity. For example, a line may be drawn, printed or painted onto the face of the patient along the midsagittal plane, for example from the nose to the upper lip, lower lip, or chin, and is thus visually coupled to a portion of the teeth during a scanning thereof in step 430. The colour, contrast, thickness of the line constitutes the geometrical structure, and this together with the part of the dental structure in the vicinity thereof, are scanned in this step, sufficient for enabling reconstruction of the geometrical structure and of enough of the dental structure to allow a match in step 450 with the first virtual model to be achieved. Alternatively, the marking may comprise any shaped symbol or geometric segment the shape of which provides information linking the marking to the midsagittal plane of the patient directly, or indirectly via any other reference plane or axis of the head of the patient.

Figure 8A:
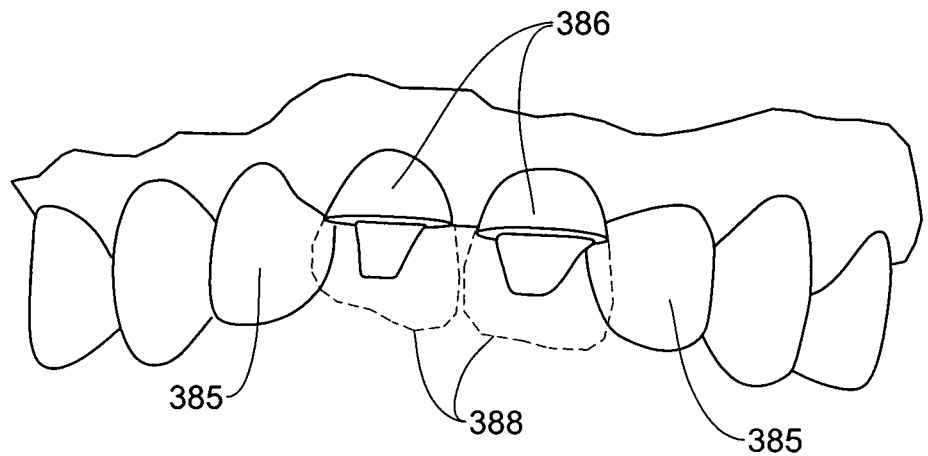
FIGS. 8(*a*) and 8(*b*) illustrate example scans provided according to an aspect of the invention.
Figure 8B:
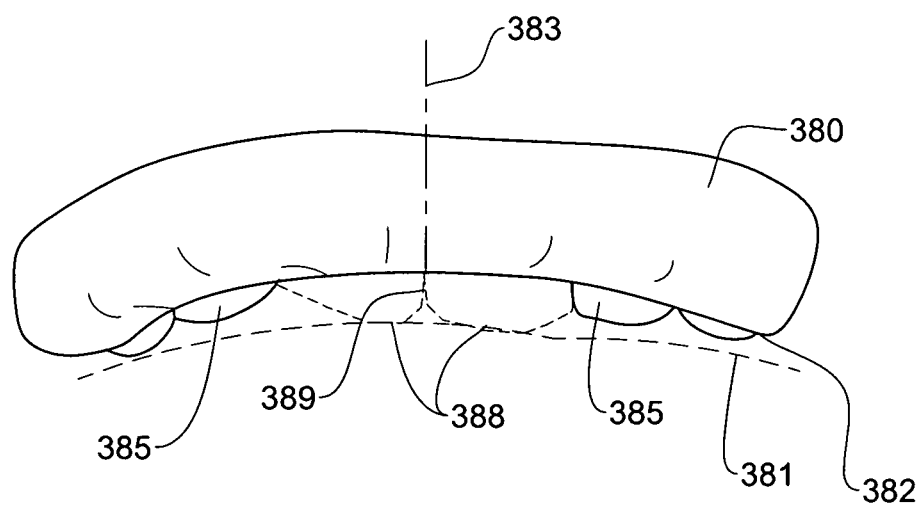

In a third embodiment of the invention, in step 430 external tissue structures, not included in the intraoral cavity, may be scanned, while visually coupled to at least a portion of the dental surfaces of the patient. For example, and referring to FIG. 8 (b), the lips, or at least the upper lip 380 of the patient is scanned together with part of the dental structure 385 visually coupled therewith, and a second virtual model of the lip 380 and dental structure 385 is reconstructed. The lips may be in a smiling position when the scan is taken. Another scan is taken to establish the first virtual model of the dental surfaces of the intraoral cavity, which also include representations of the same dental structure 385 that appear in the scan illustrated in FIG. 8(b), as well as a number of incisor teeth 386 which need crowns. According to this embodiment, the first and second virtual models are combined by registering the respective parts thereof corresponding to common dental structure 385, and the prostheses 388, marked in broken lines, can be designed in a manner to be compatible with the lip 380. For example, the prostheses may be designed such as to align the interproximal line 389 between them with the midsagittal plane 383, the position of which may be determined by studying the morphology of the lip, and/or the cusps 387 may be aligned with an imaginary arc 381 that follows the contour of the lower edge 382 of the lip 380, substantially irrespective of the position of the respective preparation or stumps of the teeth 386 or their root structures. According to this embodiment, the designer task of designing the prostheses for the anterior teeth to match the smile of the patient is greatly facilitated. The arc 381 may be an approximation to the smile line of the patient, for example.

It is to be noted that the computer system in which the virtual models are created and manipulated according to the invention does not necessarily need to be located in the same geographical location as the scanner and patient. Thus, while the scanning of the patient is usually done at a dental clinic by the dentist or other dental practitioner, the dental clinic may instead or additionally be linked to one or more dental labs, and possibly also to a dental service center via a communication means or network such as for example the Internet or other suitable communications medium such as an intranet, local access network, public switched telephone network, cable network, satellite communication system, and the like. Additionally or alternatively, the communication means may include postal or courier services, the data being communicated via a transportable medium such as an optical disc, magnetic disc and so on. In any case, once the second virtual model is created and matched with the first virtual model, the physical dental model, and other dental procedures not carried out on the actual patient, may be carried out by the dental lab which receives the required data generated by the method 400 via the communications means. The dental service center may be used for manufacturing dental hardware that requires a very high degree of precision, for example inner surfaces of prostheses that are required to match external surfaces of copings, and possibly also the copings themselves.

According to a particular embodiment of the invention, the following steps are performed:
  (a) a virtual impression of teeth is taken at a dental office, i.e., a digitized model (virtual model) of the patient's teeth is created.
  (b) The patient bites onto the bite fork of facebow apparatus 100.
  (c) The dental practitioner aligns the facebow apparatus with the patient's face (longitudinal direction).
  (d) The dental practitioner scans to provide the spatial relationship between the facebow apparatus and the patient's teeth.
  (e) The scan data is transmitted or otherwise sent to a modeling center for interpretation, and where necessary for virtual ditching to provide virtual modeling of dental surfaces that are obscured during scanning by either soft tissues and/or saliva, debris etc., for example as disclosed in WO 2007/010524 to the present Assignee and the contents of this reference are incorporated herein in their entirety.
  (f) The virtual model of the scanned data is displayed in the correct orientation with respect to the patient facial features or reference axes/planes (patient specific features).
  (g) The virtual model is sent to the dental lab for approval.
  (h) The lab approves the case, and sends the approval (or an updated interpretation of the model) to a production center, which manufactures a physical model of the teeth with features that will enable the models to be mounted onto an articulator in the required relationship with respect to the articulator hinge axis. The models may be made by CNC machining or rapid prototyping, for example.

(i) The dental lab designs the required prosthesis, coping, and so on based on the model, and taking into account the patient specific features.

(j) The physical model is sent to the lab and mated with the prosthesis and/or coping that was produced in the lap for final verification and esthetics building.

(k) The prosthesis and/or coping is sent to the dental practitioner for implantation to the patient.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed example embodiments in accordance with the invention, it will be appreciated that many changes may be made therein without departing from the spirit of the invention.

The invention claimed is:

1. A computer-implemented method for providing a spatial relationship of at least part of a dental structure of a patient with respect to a sagittal plane of the patient, comprising:
   (a) receiving digital scan data representing a virtual model of a composite of at least a part of a dental structure coupled with a geometric structure that is aligned with a sagittal plane of a patient, thereby providing a composite virtual model, wherein the digital scan data is generated by scanning the part of the dental structure coupled with the geometric structure with a suitable optical scanner; and
   (b) determining, using a computer system, a spatial relationship between the part of the dental structure and the sagittal plane of the patient based on the coupling between at least part of the dental structure and the geometric structure and the alignment of the geometric structure with the sagittal plane of the patient.

2. The method according to claim 1, wherein the geometric structure comprises a physical impression of the part of the dental structure, and step (a) further comprises optically scanning the physical impression coupled with the geometric structure to obtain a first auxiliary virtual model, and generating the composite virtual model from the first auxiliary virtual model.

3. The method according to claim 2, further comprising providing a second auxiliary virtual model representative of the part of the dental structure, registering the second auxiliary virtual model with the first auxiliary virtual model, and generating therefrom the composite virtual model.

4. The method according to claim 1, further comprising providing a virtual model of a second dental structure that includes the part of the first-mentioned dental structure, and determining, using a computer system, a spatial relationship between the second dental structure and the sagittal plane of the patient.

5. The method according to claim 1, wherein operation of the optical scanner is based on confocal imaging techniques.

6. The method according to claim 1, wherein step (a) comprises providing the geometric structure in the form of a facebow apparatus having a first facebow part coupled to a second facebow part via a coupling that enables the spatial relationship between the first facebow part and the second facebow part to be selectively adjusted, setting the first facebow part in a fixed spatial relationship with respect to the part of the dental structure, and setting the second facebow part in a fixed first facebow spatial relationship with respect to the sagittal plane of the patient.

7. The method according to claim 6, wherein the first facebow part comprises a bite plate, and wherein the coupling between the first facebow part and the second facebow part is configured for providing at least two degrees of freedom for the bite plate with respect to the second facebow part, which operates substantially as a rigid body with respect to the coupling, and wherein step (a) comprises manipulating the first facebow part with respect to the second facebow part via the coupling until the bite plate is abutted to at least one tooth arch of the patient comprising the at least part of the dental structure, while concurrently setting the second facebow part at the fixed first facebow spatial relationship with respect to the sagittal plane of the patient.

8. The method according to claim 7, wherein the at least two degrees of freedom includes a translation and a rotation of the bite plate with respect to the second facebow part.

9. The method according to claim 7, wherein the at least two degrees of freedom includes a first rotation, a second rotation, and a rotation of the bite plate with respect to the second facebow part.

10. The method according to claim 9, wherein the first rotation and the second rotation comprise respective rotational axes that are mutually orthogonal.

11. The method according to claim 6, wherein step (a) comprises generating a virtual model of a first zone of the facebow apparatus comprising at least a portion of the coupling between the first facebow part and the second facebow part that is sufficient to indicate the relative position and orientation of the biteplate with respect to the second facebow part, and providing a spatial relationship between the sagittal plane of the patient and the coupling between the first facebow part and the second facebow part.

12. The method according to claim 1, wherein the sagittal plane is a midsagittal plane of the patient, and wherein step (a) comprises providing the geometric structure in the form of a biteplate apparatus having a first biteplate part coupled to a second biteplate part via a coupling that enables an orientation between the first biteplate part and the second biteplate part to be selectively adjusted, setting the first biteplate part in a fixed spatial relationship with respect to the part of the dental structure, and setting the second biteplate part in a fixed first biteplate spatial relationship with respect to the midsagittal plane and in a fixed second biteplate spatial relationship with respect to the first biteplate part via the coupling.

13. The method according to claim 12, wherein step (a) further comprises manipulating the first biteplate part with respect to the second biteplate part via the coupling until the first biteplate part is abutted to at least one tooth arch of the patient comprising the part of the dental structure, while concurrently setting the second biteplate part at fixed the first biteplate spatial relationship with respect to the body reference.

14. The method according to claim 13, wherein step (a) further comprises generating a virtual model of a first zone of the biteplate apparatus comprising at least a portion of the coupling sufficient to indicate the relative position and orientation of the first biteplate part with respect to the second biteplate part to provide a spatial relationship between the midsagittal plane of the patient and the first biteplate part.

15. A method for providing a spatial relationship of a dental structure of a patient with respect to a sagittal plane of the patient, comprising:
   (a) coupling a geometric structure to a dental structure, wherein the geometric structure is aligned with a sagittal plane of a patient;
   (b) scanning at least a part of the dental structure coupled with the geometric structure, thereby generating a composite virtual model; and
   (c) determining a spatial relationship between the dental structure and the sagittal plane of the patient based on the composite virtual model, wherein the composite virtual model comprises data representing coupling between the dental structure and the geometric structure and the alignment of the geometric structure with the sagittal plane of the patient.

16. A system for providing a spatial relationship of a dental structure of a patient with respect to a body reference of the patient, comprising:
   at least one suitable scanner;
   a computer system configured for operating according to the method as defined in claim 1; and
   a suitable apparatus for use in providing the spatial relationship between the part of the dental structure and the sagittal plane of the patient.

* * * * *